US010220004B2

(12) United States Patent
Zink et al.

(10) Patent No.: US 10,220,004 B2
(45) Date of Patent: Mar. 5, 2019

(54) METHOD OF CONTROLLED DELIVERY USING SUB-MICRON-SCALE MACHINES

(75) Inventors: Jeffrey I. Zink, Sherman Oaks, CA (US); Courtney R. Thomas, Venice, CA (US); Monty Liong, Foster City, CA (US); Sarah Ann Henscheid, Corvallis, OR (US); Jinwoo Cheon, Seoul (KR); Jae-Hyun Lee, Seoul (KR); Daniel P. Ferris, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 1197 days.

(21) Appl. No.: 13/550,374

(22) Filed: Jul. 16, 2012

(65) Prior Publication Data
US 2013/0046274 A1 Feb. 21, 2013

Related U.S. Application Data

(60) Provisional application No. 61/507,737, filed on Jul. 14, 2011.

(51) Int. Cl.
*A61K 9/50* (2006.01)
*A61K 41/00* (2006.01)

(52) U.S. Cl.
CPC ........ *A61K 9/5094* (2013.01); *A61K 41/0028* (2013.01); *A61M 2205/0288* (2013.01); *A61M 2205/368* (2013.01)

(58) Field of Classification Search
CPC .. A61M 2205/0244; A61M 2205/0272; A61M 2205/0288; A61M 2205/057;
(Continued)

(56) References Cited

U.S. PATENT DOCUMENTS

| 5,622,684 A | 4/1997 | Pinnavaia et al. |
| 6,615,855 B2 | 9/2003 | Lopez et al. |

(Continued)

FOREIGN PATENT DOCUMENTS

| KR | 10-0924786 B1 | 11/2009 |
| WO | WO 00/76556 A2 | 12/2000 |

(Continued)

OTHER PUBLICATIONS

Thomas, et al. "Noninvasive remote-controlled release of drug molecules in vitro using magnetic actuation of mechanized nanoparticles", Jul. 2010, Journal of American Chemical Society, 2010, 132, 10623-10625.*

(Continued)

*Primary Examiner* — Bhisma Mehta
*Assistant Examiner* — Laura Schell
(74) *Attorney, Agent, or Firm* — Tom Hunter; Weaver Austin Villeneuve & Sampson LLP

(57) ABSTRACT

A method for controlled delivery of a substance into a body includes administering a plurality of containment vessels into the body, in which each of the plurality of containment vessels includes a quantity of the substance loaded therein prior to the administering; and providing a time-varying magnetic field such that the plurality of containment vessels are exposed thereto to cause a release of at least a portion of the substance from the plurality of containment vessels. Each of the plurality of containment vessels has an average outer diameter less than about 1 μm.

15 Claims, 8 Drawing Sheets

(58) Field of Classification Search
CPC ............... A61M 31/00; A61M 31/002; A61M 2205/3317; A61M 2205/368; A61K 41/0028; A61K 41/0052; A61K 9/0097; A61K 9/0009; A61K 9/5094; A61K 9/14; A61K 9/50; A61K 9/51
See application file for complete search history.

(56) References Cited

U.S. PATENT DOCUMENTS

| | | | |
|---|---|---|---|
| 6,755,621 | B2 | 6/2004 | Lopez et al. |
| 6,767,531 | B2 | 7/2004 | Fritzberg et al. |
| 6,902,806 | B2 | 6/2005 | Fujiwara et al. |
| 6,913,825 | B2 | 7/2005 | Ostafin et al. |
| 6,929,636 | B1 | 8/2005 | von Alten |
| 7,163,658 | B2 | 1/2007 | Bension |
| 7,258,874 | B2 | 8/2007 | Barbe et al. |
| 7,354,602 | B2 | 4/2008 | Barbe et al. |
| 7,354,603 | B2 | 4/2008 | Barbe et al. |
| 7,357,948 | B2 | 4/2008 | Barbe et al. |
| 7,563,451 | B2 | 7/2009 | Lin et al. |
| 9,993,437 | B2 | 6/2018 | Liong et al. |
| 2003/0152759 | A1 | 8/2003 | Chao et al. |
| 2004/0076681 | A1 | 4/2004 | Dennis et al. |
| 2005/0130167 | A1 | 6/2005 | Bao et al. |
| 2006/0154069 | A1 | 7/2006 | Lin et al. |
| 2006/0216239 | A1 | 9/2006 | Zhang et al. |
| 2007/0151038 | A1 | 7/2007 | Lai et al. |
| 2008/0031960 | A1 | 2/2008 | Wilson et al. |
| 2008/0107598 | A1 | 5/2008 | Yang et al. |
| 2008/0175992 | A1 | 7/2008 | Plieth et al. |
| 2008/0206146 | A1* | 8/2008 | Akhtari ............ A61K 47/48176 514/1.1 |
| 2009/0196826 | A1* | 8/2009 | Gao ................... A61K 9/5146 424/9.3 |
| 2010/0016610 | A1* | 1/2010 | Keinan ............... C07D 487/22 548/303.4 |
| 2010/0143263 | A1* | 6/2010 | Cheon ................ A61K 49/1836 424/9.322 |
| 2010/0255103 | A1 | 10/2010 | Liong et al. |
| 2010/0284924 | A1 | 11/2010 | Zink et al. |
| 2010/0310465 | A1 | 12/2010 | Zink et al. |
| 2011/0104073 | A1* | 5/2011 | Zeng ................... A61K 41/0052 424/9.32 |
| 2011/0268791 | A1 | 11/2011 | Liu et al. |
| 2012/0021034 | A1 | 1/2012 | Zink et al. |
| 2012/0207795 | A1 | 8/2012 | Zink et al. |
| 2016/0008283 | A1 | 1/2016 | Nel et al. |
| 2017/0095418 | A1 | 4/2017 | Zink et al. |

FOREIGN PATENT DOCUMENTS

| | | | |
|---|---|---|---|
| WO | WO-2006/015757 | A1 | 2/2006 |
| WO | WO 2006/032136 | A1 | 3/2006 |
| WO | WO-2007/010574 | A1 | 1/2007 |
| WO | WO-2007/015105 | A2 | 2/2007 |
| WO | WO-2007/131286 | A1 | 11/2007 |
| WO | WO 2009/064964 | * | 5/2009 |
| WO | WO-2009/078924 | A2 | 6/2009 |
| WO | WO-2009/094568 | A1 | 7/2009 |
| WO | WO 2009/094580 | * | 7/2009 |
| WO | WO-2009/094580 | A2 | 7/2009 |
| WO | WO 2009/097439 | * | 8/2009 |
| WO | WO-2009/097439 | A1 | 8/2009 |
| WO | WO-2010/071831 | A2 | 6/2010 |
| WO | WO 2010/078569 | A2 | 7/2010 |
| WO | WO-2012/009448 | A2 | 1/2012 |
| WO | WO 2013/012891 | A1 | 1/2013 |
| WO | WO-2014/138278 | A1 | 9/2014 |

OTHER PUBLICATIONS

Liong, et al. "Multifunctional inorganic nanoparticles for imaging, targeting, and drug delivery", ACS Nano, 2008 (2), 889-896.*

Angelos et al., S.; Khashab, N.M.; Yang, Y.-W.; Trabolsi, A.; Khatib, H.A.; Stoddart, J.F.; Zink, J.I. *J. Am. Chem. Soc.* 2009, 131, 12912-12914.

Aznar, E.; Marcos, M.D.; Martinez-Manez, R.; Sancenon, F.; Soto, J.; Amoros, P.; Guillem, C. *J. Am. Chem. Soc.* 2009, 131, 6833-6843.

Bernardos, A.; Aznar, E.; Marcos, M.D.; Martinez-Manez, R.; Sancenon, F.; Soto, J.; Barat, J.M.; Amoros, P. *Angew. Chem. Int. Ed.* 2009, 48, 5884-5887.

Coti, K.K.; Belowich, M.E.; Liong, M.; Ambrogio, M.W.; Lau, Y.A.; Khatib, Ha.; Zink, J.I.; Khashab, N.M.; Stoddart, J.F. 2009, 1, 16-39.

Derfus, A.M.; Maltzahn, G.; Harris, T.J.; Duza, T.; Vecchio, K.S.; Ruoslahti, E.; Bhatia, S.N. *Adv. Mater.* 2007, 19, 3932-3936.

Ferris, D.P.; Zhao, Y.-L.; Khashab, N.M.; Khatib, H.A.; Stoddart, J.F.; Zink, J.I. *J. Am. Chem. Soc.* 2009, 131, 1686-1688.

Fortin, J.-P.; Wilhelm, C.; Servals, J.; Menager, C.; Bacri, J.-C.; Gazeau, F. *J. Am. Chem. Soc.* 2007, 129, 2628-2635.

Fusaro, L.; Locci, E.; Lai, A.; Luhmer, M. *J. Phys. Chem. B* 2008, 112, 15014-15020.

Giri, S.; Trewyn, B.G.; Stellmaker, M.P.; Lin, V.S.-Y. *Angew Chem. Int. Ed.* 2005, 44, 5038-5044.

Hu, S.-H.; Chen, S.-Y.; Liu, D.-M.; Hsaio, C.-S. *Adv. Mater.* 2008, 20, 2690-2695.

Jang, J.-T.; Nah, H.; Lee, J.-H.; Moon, S.H.; Kim, M.G.; Cheon, J. *Angew. Chem., Int. Ed.* 2009, 48, 1234-1238.

Jun, Y.-W.; Lee, J.-H.; Cheon, *J. Angew. Chem. Int. Ed.* 2008, 47, 5122-5135.

Kim, K. *Chem. Soc. Rev.* 2002, 31, 96-107.

Lai, C.-Y.; Trewyn, B.G.; Jeftinija, D.M.; Jeftinija, K.; Xu, S.; Jeftinija, S.; Lin, V.S.-Y. *J. Am. Chem. Soc.* 2003, 125, 4451-4459.

Laurent, S.; Forge, D.; Port, M.; Roch, A.; Robic, C.; Elst, L.V.; Muller, R.N.; *Chem. Rev.* 2008, 108, 2064-2110.

Lee, J.-H.; Huh, Y.-M.; Jun, Y.-W.; Seo, J.-W.; Jang, J.-T.; Song, H.-T.; Kim, S.; Cho, E.-J.; Yoon, H.-G.; Suh, J.-S.; Cheon, *J. Nat. Med.* 2007, 13, 95-99.

Leung, K.C.-F.; Nguyen, T.D.; Stoddart, J.F.; Zink, J.I. *Chem. Mater.* 2006, 18, 5919-5928.

Lin, Y.-S.; Tsai, C.-P.; Huang, H.-Y.; Kuo, C.-T.; Hung, Y.; Huang, D.-M.; Chen, Y.-C.; Mou, C.-Y. *Chem. Mater.* 2005, 17, 4570-4573.

Lin, Y.-S.; Wu, S.-H.; Hung, Y.; Chou, Y.-H.; Chang, C.; Lin, M.-L.; Tsai, C.-P.; Mou, C.-Y. *Chem. Mater.* 2006, 18, 5170-5172.

Liong, M.; Lu, J.; Kovochich, M.; Xia, T.; Ruehm, S.G.; Nel, A.E.; Tamanoi, F.; Zink, J.I. *ACS Nano* 2008, 2, 889-896.

Liu, R.; Zhao, X.; Wu, T.; Feng, P. *J. Am. Chem. Soc.* 2008, 130, 14418-14419.

Lu, J.; Liong, M.; Zink, J.I.; Tamanoi, F. *Small* 2007, 3, 1341-1346.

Mal, N.K.; Fujiwara, M.; Tanaka, Y. *Nature* 2003, 421, 350-353.

Masson, E.; Lu, X.; Ling, X.; Patchell, D.L. *Org. Lett.* 2009, 11, 3798-3801.

Mock, W.L. *Top. Curr. Chem.* 1995, 175, 1-24.

Nguyen, T.D.; Leung, K.C.-F.; Liong, M.; Liu, Y.; Stoddart, J.F.; Zink, J.I. *Adv. Funct. Mater.* 2007, 17, 2101-2110.

Nguyen, T.D.; Tseng, H.-R.; Celestre, P.C.; Flood, A.H.; Liu, Y.; Stoddart, J.F.; Zink, J.I. *Proc. Natl. Acad. Sci. U.S.A.* 2005, 102, 10029-10034.

Park, C.; Lee, K.; Kim, C. *Angew. Chem. Int. Ed.* 2009, 48, 1275-1278.

Park, C.; Oh, K.; Lee, S.C.; Kim, C. *Angew. Chem. Int. Ed.* 2007, 46, 1455-1457.

Rosenholm, J.M.; Meinander, A.; Peuhu, E.; Niemi, R.; Eriksson, J.E.; Sahlgren, C.; Lind, M. *ACS Nano* 2009, 3, 197-206.

Saha, S.; Johansson, E.; Flood, A.H.; Tseng, H.-R.; Zink, J.I.; Stoddart, J.F. *Chem. Euro. J.* 2005, 11, 6846-6858.

Schlossbauer, A.; Kecht, J.; Bein, T. *Angew. Chem. Int. Ed.* 2009, 48, 3092-3095.

Slowing, I.; Trewyn, B.G.; Lin, V.S.-Y. *J. Am. Chem. Soc.* 2006, 128, 14792-14793.

Slowing, I.; Trewyn, B.G.; Lin, V.S.-Y. *J. Am. Chem. Soc.* 2007, 129, 8845-8849.

Vallet-Regi, M.; Balas, F.; Arcos, D. *Angew. Chem., Int. Ed.* 2007, 46, 7548-7558.

(56) References Cited

OTHER PUBLICATIONS

Vivero-Escoto, J.L.; Slowing, I.I.; Wu, C.-W.; Lin, V.S.-Y. *J. Am. Chem. Soc.* 2009, 131, 3462-3463.

Weissleder, R.; Moores, A.; Mahmood, U.; Bhorade, R.; Benveniste, H.; Chiocca, E.A.; Basilion, J.P. *Nat. Med.* 2000, 6, 351-354.

Zhao, Y.; Trewyn, B.G.; Slowing, I.I.; Lin, V.S.-Y. *J. Am. Chem. Soc.* 2009, 131, 8398-8400.

Zhu, Y.; Fujiwara, M. *Angew. Chem. Int. Ed.* 2007, 46, 2241-2244.

U.S. Office Action (Restriction Requirement), dated Dec. 5, 2011 issued in U.S. Appl. No. 12/746,375.

U.S. Office Action, dated Mar. 14, 2012, issued in U.S. Appl. No. 12/746,375.

U.S. Final Office Action, dated Nov. 26, 2012, issued in U.S. Appl. No. 12/746,375.

U.S. Office Action, dated May 8, 2014, issued in U.S. Appl. No. 12/746,375.

U.S. Final Office Action, dated Mar. 2, 2015, issued in U.S. Appl. No. 12/746,375.

U.S. Office Action, dated Jan. 6, 2016, issued in U.S. Appl. No. 12/746,375.

U.S. Office Action, dated Jul. 10, 2012, issued in U.S. Appl. No. 12/812,359.

U.S. Office Action, dated Feb. 14, 2013, issued in U.S. Appl. No. 12/812,359.

U.S. Final Office Action, dated Jul. 26, 2013, issued in U.S. Appl. No. 12/812,359.

U.S. Final Office Action (Letter Restarting Period for Response), dated Jul. 29, 2013, issued in U.S. Appl. No. 12/812,359.

U.S. Office Action (Before the Patent Trial and Appeal Board, Examiner's Answer to Appeal Brief), dated Aug. 28, 2014, issued in U.S. Appl. No. 12/812,359.

U.S. Office Action (Restriction Requirement), dated May 21, 2012, issued in U.S. Appl. No. 12/841,331.

U.S. Office Action, dated Aug. 13, 2012, issued in U.S. Appl. No. 12/841,331.

U.S. Office Action, dated Apr. 30, 2013, issued in U.S. Appl. No. 12/841,331.

U.S. Final Office Action, dated Dec. 26, 2013, issued in U.S. Appl. No. 12/841,331.

U.S. Office Action, dated Dec. 10, 2014, issued in U.S. Appl. No. 12/841,331.

U.S. Final Office Action, dated May 13, 2015, issued in U.S. Appl. No. 12/841,331.

U.S. Office Action, dated Jan. 20, 2016, issued in U.S. Appl. No. 12/841,331.

U.S. Office Action (Restriction Requirement), dated Nov. 26, 2012, issued in U.S. Appl. No. 13/140,714.

U.S. Office Action, dated May 10, 2013, issued in U.S. Appl. No. 13/140,714.

U.S. Final Office Action, dated Feb. 28, 2014, issued in U.S. Appl. No. 13/140,714.

U.S. Office Action, dated Mar. 13, 2015, issued in U.S. Appl. No. 13/140,714.

U.S. Final Office Action, dated Nov. 20, 2015, issued in U.S. Appl. No. 13/140,714.

U.S. Office Action (Restriction Requirement), dated Mar. 29, 2013, issued in U.S. Appl. No. 13/428,830.

U.S. Office Action, dated Oct. 3, 2013, issued in U.S. Appl. No. 13/428,830.

U.S. Final Office Action, dated Aug. 1, 2014, issued in U.S. Appl. No. 13/428,830.

U.S. Office Action, dated Dec. 5, 2014, issued in U.S. Appl. No. 13/428,830.

U.S. Final Office Action, dated Jul. 23, 2015, issued in U.S. Appl. No. 13/428,830.

U.S. Office Action, dated May 16, 2016, issued in U.S. Appl. No. 13/428,830.

PCT International Search Report and Written Opinion dated May 14, 2009 issued in PCT/US08/13476.

PCT International Preliminary Report on Patentability and Written Opinion dated Jun. 8, 2010 issued in PCT/US08/13476.

PCT International Search Report and Written Opinion dated May 19, 2009 issued in PCT/US09/031872.

PCT International Preliminary Report on Patentability dated Aug. 5, 2010 issued in PCT/US09/031872.

PCT International Search Report and Written Opinion dated Mar. 27, 2009 issued in PCT/US2009/032451.

PCT International Preliminary Report on Patentability and Written Opinion dated Aug. 12, 2010 issued in PCT/US2009/032451.

PCT International Search Report and Written Opinion dated May 28, 2009 issued in PCT/US2009/031891.

PCT International Preliminary Report on Patentability and Written Opinion dated Aug. 5, 2010 issued in PCT/US2009/031891.

PCT International Search Report dated Sep. 3, 2010 issued in PCT/US2009/068816.

PCT International Preliminary Report on Patentability and Written Opinion dated Jun. 30, 2011 issued in PCT/US2009/068816.

PCT International Search Report dated Apr. 6, 2012 issued in PCT/US2011/043874.

PCT International Preliminary Report on Patentability dated Jan. 24, 2013 issued in PCT/US2011/043874.

PCT International Search Report and Written Opinion dated Jun. 24, 2014 issued in PCT/US2014/020857.

PCT International Report on Patentability and Written Opinion dated Sep. 17, 2015 issued in PCT/US2014/020857.

Tamanoi (2006) Nanodelivery: Towards controlled release of anti-cancer drugs. Oral Presentation on Dec. 6, 2006 (see NanoBio—Tokyo 2006 Program), 7 pages. Abstract provided in *Proceedings of UT Symposium on NanoBio Integration Program* and Abstract provided.

Stöber et al., (1968) "Controlled growth of monodisperse silica spheres in the micron size range," *J Colloid and Interface Sci.*, 26:62-69.

Angelos et al., (2007) "Photo-Driven Expulsion of Molecules from Mesostructured Silica Nanoparticles," *J Phys Chem C*, 111:6589-6592.

Nguyen et al., (2007) "Design and optimization of molecular nanovalves based on redox-switchable bistable rotaxanes," *Journal of the American Chemical Society*, 129(3):626-634.

Abigerges et al., (1995) *Clin. Oncol.*, 13:210-221.

Al Shamsi et al., (2010) *Chem. Res. Toxicol.*, 23:1796-1805.

Alvaro et al., (2005) *Chem. Mater.*, 17:4958-4964.

Angelos et al., (2007) "Mesostructured silica supports for functional materials and molecular machines," *Adv. Funct. Mater.*, 17:2261-2271.

Angelos et al., (2008) "PH-Responsive supramolecular nanovalves based on cucurbit[6] uril pseudorotaxanes," *Agnew, Chem. Int. Ed.*, 47:2222-2226.

Aprahamian et al., (2007) "A Clicked Bistable [2]Rotaxane," *Org. Lett.*, 9(7):1287-1290.

Arnida et al., (2009) "Cellular Uptake and Toxicity of Gold Nanoparticles in Prostate Cancer Cells: A Comparative Study of Rods and Spheres," *J. Appl. Toxicol.*, 30:212-217.

Arnold et al., (2004) "Activation of Integrin Function by Nanopatterned Adhesive Interfaces," *ChemPhysChem*, 5:383-388.

Arola et al., (2000) "Acute Doxorubicin Cardiotoxicity Involves Cardiomyocyte Apoptosis," *Cancer Res.*, 60:1789-1792.

Arruebo et al., (2006) "Development of Magnetic Nanostructured Silica-Based Materials as Potential Vectors for Drug-Delivery Applications," *Chem. Mater.*, 18:1911-1919 (Published online Mar. 14, 2006).

Arruebo et al., (2006) *Nanotechnology*, 17:4057-4064 (Published Jul. 18, 2006).

Bagwe et al., (2006) "Surface Modification of Silica Nanoparticles to Reduce Aggregation and Nonspecific Binding," *Langmuir*, 22:4357-4362 (Apr. 25, 2006).

Barbe et al., (2004) "Silica particles: A novel drug-delivery system," *Adv. Mater.*, 16:1959-1966.

Beck et al., (1992) "A new family of mesoporous molecular sieves prepared with liquid crystal templates," *J. Am. Chem. Soc.*, 114:10834-10843.

(56) References Cited

OTHER PUBLICATIONS

Belloc et al., (1994) "A Flow Cytometric Method Using Hoechst 33342 and Propidium Iodide for Simultaneous Cell Cycle Analysis and Apoptosis Determination in Unfixed Cells," *Cytometry*, 17:59-65.
Berry et al., (2005) "Self-Assembly of nanoparticles on live bacterium: An avenue to Fabricate Electronic Devices," *Angew. Chem., Int. Ed.*, 44:6668-6673.
Besson et al., (2005) *J. Mater. Chem.*, 15:803-809.
Bettio et al., (2006) *J. Nucl. Med.*, 47:1153-1160.
Bharali et al., (2005) *Proc. Natl. Acad. Sci. USA.*, 102:11539-11544.
Blow et al., (2007) *Nature*, 450:1117-1120.
Bonoiu et al., (2009) *Proc. Natl. Acad. Sci. USA.*, 106:5546-5550.
Borm et al., (2006) *Toxicol. Sci.*, 90:23-32.
Botella et al., (2007) "Single gold nanoparticles encapsulated in monodispersed regular spheres of mesostructured silica produced by pseudomorphic transformation," *Chem. Mater*, 19:1979-1983.
Boussif et al., (1995) *Proc. Natl. Acad. Sci. U.S.A.*, 92:7297-7301.
Braunschweig et al., (2007) *Chem. Asian J.*, 2:634-637.
Brigger et al., (2002) "Nanoparticles in cancer therapy and diagnosis," *Advanced Drug Delivery Reviews*, 54:631-651.
Brust et al., (1994) "Synthesis of Thiol-Derivatised Gold Nanoparticles in a Two-Phase Liquid-Liquid System," *Chem. Commun.* 801-802.
Butler et al., (2006) "Purified Integrin Adhesion Complexes Exhibit Actin-Polymerization Activity," *Curr. Biol.*, 16:242-251.
Cai et al., (2001) "Dilute Solution Routes to Various Controllable Morphologies of MCM-41 Silica with a Basic Medium," *Chem. Mater.*, 13(2):258-263.
California Nano Systems Institute 2005 Annual Research Report: "Powered Artificial Nano-Machines: Molecular Valves and Impellers," URL:http://www.cnsi.ucla.edu/spheres/ResReport-2005.pdf [retrieved on Jul. 8, 2010], p. 51.
Canonico et al., (1969) *J. Cell Biol.*, 43:367-371.
Cauda et al., (2010) *Micropor. Mesopor. Mat.*, 132:60-71.
Cavalcanti-Adam et al., (2007) "Cell Spreading and Focal Adhesion Dynamics Are Regulated by Spacing of Integrin Ligands," *Biophys. J.*, 92:2964-2974.
Celano et al., (2004) "Cytotoxic effects of Gemcitabine-loaded liposomes in human anaplastic thyroid carcinoma cells," BMC Cancer, 4(63):5 pages.
Champion et al., (2006) "Role of Target Geometry in Phagocytosis," *Proc. Natl. Acad. Sci. U.S.A.*, 103:4930-4934.
Champion et al., (2007) "Making Polymeric Micro- and Nanoparticles of Complex Shapes," *Proc. Natl. Acad. Sci. U.S.A.*, 104:11901-11904.
Champion et al., (2007) "Particle shape: A New Design Parameter for Micro- and Nanoscale Drug Delivery Carriers," *J. Control. Release*, 121:3-9.
Chen et al., (1988) *J. Biol. Chem.*, 263(18):8754-8758.
Chen et al., (1996) "Requirement of CDC42 for *Salmonella*-Induced Cytoskeletal and Nuclear Responses," *Science*, 274:2115-2118.
Chen et al., (2007) "Immuno Gold Nanocages with Tailored Optical Properties for Targeted CH Photothermal Destruction of Cancer Cells," *Nano Lett.*, 7(5):1318-1322 (Published online Apr. 15, 2007).
Chen et al., (2008) "Functional $Fe_3O_4/TiO_2$ core/shell magnetic nanoparticles as photokilling agents for pathogenic bacteria," *Small*, 4(4):485-491.
Chen et al., (2009) *Small*, 5:2673-2677.
Chithrani et al., (2006) "Determining the Size and Shape Dependence of Gold Nanoparticle Uptake into Mammalian Cells," *Nano Lett.*, 6:662-668.
Chithrani et al., (2007) "Elucidating the Mechanism of Cellular Uptake and Removal of Protein-Coated Gold Nanoparticles of Different Sizes and Shapes," *Nano Lett.*, 7:15421550.
Cho et al., (2008) *Clin. Cancer Res.*, 14:1310-1316.
Chung et al., (2007) *Biomaterials*, 28:2959-2966 (Published online Mar. 19, 2007).
Clottens et al., (1997) *Occup. Environ. Med.*, 54:376-387.
Conner et al., (2003) "Regulated Portals of Entry into the Cell," *Nature*, 422:37-44.
Corot et al., (2006) "Recent Advances in Iron Oxide Nanocrystal Technology for Medical Imaging," *Adv. Drug Delivery Rev.*, 58:1471-1504.
Coti et al., (2009) "Mechanised Nanoparticles for Drug Delivery," *Nanoscale*, 1:16-39.
Cunha et al., (2002) *Mutagenesis*, 17(2):141-147.
Darbre et al., (2006) *Chem. Res.*, 39:925-934.
Darzynkiewicz et al., (1997) "Cytometry in Cell Necrobiology: Analysis of Apoptosis and Accidental Cell Death (Necrosis)," *Cytometry*, 27:1-20.
Dausend et al., (2008) "Uptake Mechanism of Oppositely Charged Fluorescent Nanoparticles in HeLa Cells," *Macromol. Biosci.*, 8:1135-1143.
Davis et al., (2008) "Nanoparticle therapeutics: an emerging treatment modality for cancer," *Nature Reviews Discovery*, 7:771-782.
Davis et al., (2009) *Mol. Pharm.*, 6:659-668.
De Smedt et al., (2000) *Pharmaceutical Research*, 17(2):113-126.
de Wolf et al., (2007) *Int. J. Pharm.*, 331:167-175.
Decuzzi et al., (2008) "The Receptor-Mediated Endocytosis of Nonspherical Particles," *Biophys. J.*, 94:3790-3797.
Decuzzi et al., (2010) "Size and Shape Effects in the Biodistribution of Intravascularly Injected Particles," *J. Control. Release*, 141:320-327.
Denny et al., (2004) "Tumor-activated Prodrugs—A New Approach to Cancer Therapy," *Cancer Invest.*, 22(4):604-619.
Dhanikula et al., (2006) "Synthesis and Evaluation of Novel Dendrimers with a Hydrophilic Interior as Nanocarriers for Drug Delivery," *Bioconjugate Chem.*, 17:29-41.
Dharmawardhane et al., (2000) "Regulation of Macropinocytosis by p21-activated Kinase-1," *Mol. Biol. Cell*, 11:3341-3352.
Dietrich et al., (2001) "Effects of Particle Size and Molecular Weight of Polyethylenimine on Properties of Nanoparticulate Silicon Dispersions," *J. Am. Ceram. Soc.*, 84(4):806-812.
Dichtel et al., (2006) *J. Am. Chem. Soc.*, 128(32):10388-10390.
Discher et al., (2005) "Tissue Cells Feel and Respond to the Stiffness of Their Substrate," *Science*, 310:1139-1143.
Doshi et al., (2010) "Macrophages Recognize Size and Shape of Their Targets," *PLoS ONE*, 5:e10051.
Duan et al., (2007) *J. Am. Chem. Soc.*, 129:3333-3338.
Duncan et al., (2005) *Endocr-Relat. Cancer.*, 12:S189-S199.
Duncan et al., (2006) *J. Drug Target.*, 14:337-341.
Elbakry et al., (2009) *Nano Lett.*, 9:2059-2064.
Fan et al., (2004) "Self-Assembly of Ordered, Robust, Three-Dimensional Gold Nanocrystal/Silica Arrays," *Science*, 304:567-571.
Fan et al., (2006) "Ordered Nanocrystal/Silica Particles Self-Assembled from Nanocrystal Micelles and Silicate," *Chem. Commun.*, 2323-2325 (Published online Mar. 29, 2006).
Fang et al., (2004) "Factors and Mechanism of "EPR" Effect and the Enhanced Antitumor Effects of Macromolecular Drugs Including SMANCS," *In Polymer Drugs in the Clinical Stage*, Springer US, 519:29-49.
Fang et al., (2011) *Adv. Drug Delivery Rev.*, 63:136-151.
Faris et al., (1991) *Clin. Phys. Physiol. Meas.*, 12(4):353-358.
Febvay et al., (2010) *Nano Lett.*, 10:2211-2219.
Fenske et al., (2001) *Curr. Opin. Mol. Ther.*, 3(2):153-158.
Ferrari et al., (2005) *Nat. Rev. Cancer*, 5:161-171.
Ferris et al., (2009) "Light-Operated Mechanized Nanoparticles," *J. Am. Chem. Soc.*, 131:1686-1688.
Finnie et al., (2009) *J. Sol-Gel. Sci. Techn.*, 49:12-18.
Fiorentini et al., (2001) "Activation of Rho GTPases by Cytotoxic Necrotizing Factor 1 Induces Macropinocytosis and Scavenging Activity in Epithelial Cells," *Mol. Biol. Cell*, 12:2061-2073.
Florea et al., (2002) *AAPS PharmSci.*, 4(3)article 12:E12, 11 pages.
Frangioni et al., (2003) "In vivo near-infrared fluorescence imaging," *Curr. Opin. Chem*, 7:626-634.
Frisch et al., (1996) "Nanocomposites Prepared by Threading Polymer Chains through Zeolites, Mesoporous Silica, or Silica Nanotubes," *Chem. Mater.*, 8(8):1735-1738.
Fuchs et al., (2006) *Cancer Treat. Rev.*, 32:491-503.

(56) References Cited

OTHER PUBLICATIONS

Fuller et al., (2008) "Intracellular delivery of core-shell fluorescent silica nanoparticles," *Biomaterials*, 29:1526-1532.
Gamen et al., (2000) "Doxorubicin Treatment Activates a Z-VAD-Sensitve Caspase, Which Causes ΔΨm Loss, Caspase-9 Activity, and Apoptosis in Jurkat Cells," *Exp. Cell Res.*, 258:223-235.
Gao et al., (2004) "In Vivo Cancer Targeting and Imaging with Semiconductor Quantum Dots," *Nat. Biotechnol.*, 22(8):969-976.
Garg et al., (2002) "Editorial: Hepatic Steatosis, Insulin Resistance, and Adipose Tissue Disorders," *J. Clin. Endocrinol. Metab.*, 87:3019-3022.
Geiger et al., (2009) "Environmental Sensing Through Focal Adhesions," *Nat. Rev. Mol. Cell Biol.*, 10:21-33.
Gemeinhart et al., (2005) *Biotechnol. Prog.*, 21:532-537.
Georganopoulou et al., (2005) "Nanoparticle-Based Detection in Cerebral Spinal Fluid of a Soluble CA Pathogenic Biomarker for Alzheimer's Disease," *Proc. Natl. Acad. Sci. USA* 102(7):2273-2276.
Gerion et al., (2001) "Synthesis and Properties of Biocompatible Water-Soluble Silica-Coated CdSe/ZnS Semiconductor Quantum Dots," *J. Phys. Chem. B*, 105(37):8861-8871.
Glass et al., (2003) "Micro-Nanostructured Interfaces Fabricated by the Use of Inorganic Block Copolymer Micellar Monolayers as Negative Resist for Electron-Beam Lithography," *Adv. Funct. Mater.*, 13:569-575.
Glass et al., (2004) "Block Copolymer Micelle Nanolithography on Non-Conductive Substrates," *New J. of Phys.*, 6:101, 18 pages.
Gobin et al., (2007) "Near-Infrared Resonant Nanoshells for Combined Optical Imaging and Photothermal Cancer Therapy," *Nano Lett.*, 7(7):1929-1934 (Published online Jun. 6, 2007).
Godbey et al., (1999) *Proc. Natl. Acad. Sci. USA*, 96:5177-5181.
Gopin et al., (2006) *Bioconjug. Chem*, 17:1432-1440.
Gorelikov et al., (2008) "Single-step coating of mesoporous silica on cetyltrimethyl ammonium bromide-capped nanoparticles," *Nano Letters*, 8(1):369-373.
Gottesman et al., (2002) *Annu. Rev. Med.*, 53:615-627.
Gratton et al., (2008) "The Effect of Particle Design on Cellular Internalization Pathways," *Proc. Natl. Acad. Sci. USA.*, 105:11613-11618.
Grün et al., (1997) "The Synthesis of Micrometer- and Submicrometer-Size Spheres of Ordered Mesoporous Oxide MCM-41," *Adv. Mater.*, 9(3):254-257.
Guiotto et al., (2004) *J. Med. Chem.*, 47:1280.
Guo et al., (2008) "Biocompatible, luminescent silver@phenol formaldehyde resin core/shell nanospheres: Large-scale synthesis and application for in vivo bioimaging," *Advance Functional Materials*, 18:872-879.
Gupta et al. (2005) "Synthesis and surface engineering of iron oxide nanoparticles for biomedical applications," *Biomaterials*, 26:3995-4021.
Han et al., (1999) *J. Am. Chem. Soc.*, 121(142):9897-9898.
Han et al., (2008) "Reverse microemulsion-mediated synthesis of silica-coated gold and silver nanoparticles," *Langmuir*, 24:5842-5848.
Harada, (2001) "Cyclodextrin-Based Molecular Machines," *Accounts of Chemical Research*, 34:456-464.
Harvey et al., (1998) *Amer. Zool.*, 38:426-441.
Hasegawa et al., (1996) "Involvement of CPP32/Yama(-like) Proteases in Fas-mediated Apoptosis," *Cancer Res*, 56:1713-1718.
Hayakawa et al., (2008) "Actin Stress Fibers Transmit and Focus Force to Activate Mechanosensitive Channels," *J. Cell Sci*, 121:496-503.
Hayek et al., (2005) *N. Engl. J. Med.*, 352:2456-2457.
He et al., (2011) *Small*, 7:271-280.
Hernandez et al., (2001) *J. Am. Chem. Soc.*, 123:1248-1249.
Hernandez et al., (2004) *Am. Chem. Soc.*, 126:3370-3371.
Hertzberg et al., (1989) *J. Med. Chem.* 32(3):715-729.
Hetrick et al., (2008) "Bactericidal efficacy of nitric oxide-releasing silica nanoparticles," *ACS Nano*, 2(2):235-246.
Heuser et al., (1989) *J. Cell Biol.*, 108:389-400.
Hillaireau et al., (2009) "Nanocarriers' Entry into the Cell: Relevance to Drug Delivery," *Cell. Mol. Life Sci.*, 66:2873-2896.
Hiramatsu et al., (2004) "A Simple Large-Scale Synthesis of Nearly Monodisperse Gold and Silver Nanoparticles with Adjustable Sizes and with Exchangeable Surfactants," *Chem. Mater.*, 16(13):2509-2511.
Hirano et al., (1979) *Makromol. Chem.*, 180:1125-1131.
Ho et al., (2004) "Nanoseparated polymeric networks with multiple antimicrobial properties," *Adv. Mater*, 16(12):957-961.
Höbel et al., (2008) *Eur. J. Pharm. Biopharm.*, 70:29-41.
Hoet et al., (1999) *Toxicol. Sci.*, 52:209-216.
Hoet et al., (2001) *Toxicol. Appl. Pharmacol.*, 175:184-190.
Hu et al., (2010) "Nanoparticle-assisted combination therapies for effective cancer treatment," *Therapeutic Delivery*, 1(2):323-334.
Huang et al., (1998) *Langmuir*, 14:7331-7333.
Huang et al., (2006) "Cancer Cell Imaging and Photothermal Therapy in the Near-Infrared Region by CG Using Gold Nanorods," *J. Am. Chem. Soc.*, 128(6):2115-2120 (Published online Jan. 21, 2006).
Huang et al., (2010) "The Effect of the Shape of Mesoporous Silica Nanoparticles on Cellular Uptake and Cell Function," *Biomaterials*, 31:438-448.
Hughes (2005) "Nanostructure-mediated drug delivery," *Nanomedicine: Nanotechnology, Biology, and Medicine*, 1:22-30.
Huh et al., (2003) *Chem. Mater.*, 15:4247-4256.
Iyer et al., (2006) *Drug Discov. Today*, 11:812-818.
Jabr-Milane et al., (2008) *Cancer Treat. Rev.*, 34:592-602.
Jana et al., (2004) "Size- and Shape-Controlled Magnetic (Cr, Mn, Fe, Co, Ni) Oxide Nanocrystals via a Simple and General Approach," *Chem. Mater.*, 16(20):3931-3935.
Jana et al., (2007) "Synthesis of Water-Soluble and Functionalized Nanoparticles by Silica Coating," *Chem Mater*, 19:5074-5082.
Jiang et al., (2006) "Aerosol-Assisted Self-Assembly of Single-Crystal Core/Nanoporous Shell Particles as Model Controlled Release Capsules," *J. Am. Chem. Soc.*, 128:4512-4513 (Published online Mar. 16, 2006).
Jin et al., (2007) "Toxicity of Luminescent Silica Nanoparticles to Living Cells," *Chem. Res. Toxicol.* 20(8):1126-1133 (Published online Jul. 13, 2007).
Judge et al., (2006) *Mol. Ther.*, 13:494-505.
Jun et al., (2005) "Nanoscale Size Effect of Magnetic Nanocrystals and Their.Utilization for Cancer Diagnosis via Magnetic Resonance Imaging," *J. Am. Chem. Soc.*, 127:5732-5733.
Kahn et al., (2010) "Macropinocytotic Uptake and Infection of Human Epithelial Cells with Species B2 Adenovirus Type 35," *J. Virol.*, 84:5336-5350.
Kam et al., (2005) "Carbon Nanotubes as Multifunctional Biological Transporters and Near-Infrared Agents for Selective Cancer Cell Destruction," *Proc. Natl. Acad. Sci. USA*, 102(33): 11600-11605.
Kandutsch et al., (2008) *Eur. J. Surg. Oncol.*, 34:1231-1236.
Karmali et al., (2009) "Targeting of albumin-embedded paclitaxel nanoparticles to tumors," *Nanomedicine*, 5:73-82.
Kataoka et al., (2001) *Adv. Drug Delivery Rev.*, 47:113-131.
Kaul et al., (2004) "Biodistribution and Targeting Potential of Poly(ethylene glycol)-modified Gelatin Nanoparticles in Subcutaneous Murine Tumor Model," *J. Drug Target.*, 12:585-591.
Kawano et al., (2006) *J. Controlled Release*, 111:382-389.
Keane et al., (1998) *J. Urol.*, 160:252-256.
Kim et al., (2006) "Magnetic Fluorescent Delivery Vehicle Using Uniform Mesoporous Silica Spheres Embedded with Monodisperse Magnetic and Semiconductor Nanocrystals," *J. Am. Chem. Soc.*, 128:688-689 (Published online Dec. 31, 2005).
Kim et al., (2006) *J. Vet. Sci.*, 7(4):321-326.
Kim et al., (2008) *Angew. Chem., Int. Ed.*, 47:8438-8441.
Kircheis et al., (1999) *J. Gene. Med.*, 1:111-120.
Kircheis et al., (2002) *Cancer Gene. Ther.*, 9:673-680.
Kneuer et al., (2000) *Bioconjugate Chem.*, 11:926-932.
Kobler et al., (2008) "Colloidal suspensions of functionalized mesoporous silica nanoparticles," *ACS Nano*, 2(4):791-799.
Kocer et al., (2005) *Science*, 309:755-758.
Kohler et al., (2006) "Methotrexate-Immobilized Poly(ethylene glycol) Magnetic Nanoparticles for MR Imaging and Drug Delivery," *Small*, 2(6):785-792.

(56) References Cited

OTHER PUBLICATIONS

Kónya et al., (2003) "Synthetic Insertion of Gold Nanoparticles into Mesoporous Silica," *Chem Mater*, 15(6): 1242-1248.
Kremer et al., (1996) "Computer Visualization of Three-dimensional Image Data Using IMO," *J. Struct. Biol*, 116:71-76.
Kresge et al., (1992) "Ordered mesoporous molecular sieves synthesized by a liquid-crystal template mechanism," *Nature*, 359:710-712.
Kumar et al., (2008) "Silver-nanoparticle-embedded antimicrobial paints based on vegetable oil," *Nat. Mater.*, 7:236-241.
Kunath et al., (2002) *Pharm. Res.*, 19:810-817.
Kursa et al., (2003) *Bioconjugate Chem.*, 14:222-231.
Lang et al., (2004) "A Fast and Efficient ion-Exchange Procedure to Remove Surfactant Molecules from MCM-41 Materials," *Chem. Mater.*, 16:1961-1966.
Lee et al., (1994) "Delivery of Liposomes into Cultured KB Cells via Folate Receptor-Mediated Endocytosis," *J. Biol. Chem.*, 269(5):3198-3204.
Lee et al., (2005) *Nat. Biotechnol.*, 23(12): 1517-1526.
Lee et al., (2006) "Dual-Mode Nanoparticle Probes for High-Performance Magnetic Resonance and Fluorescence Imaging of Neuroblastoma," *Angew. Chem., Int. Ed.*, 118:8340-8342 (Published online Nov. 14, 2006).
Lee et al., (2009) "Shaping Nano-/Micro-particles for Enhanced Vascular Interaction in Laminar Flows," *Nanotechnology*, 20:495101, 12 pp.
Lee et al., (2009) *Adv. Funct. Mater.*, 19:215-222.
Lee et al., (2010) *Angew. Chem. Int. Ed.*, 49:8214-8219.
Lee et al., (2010) *Mol. Pharm.*, 7:1195-1208.
Li et al., (1999) "Preparation of $Ag/SiO_2$ nanosize composites by a reverse micelle and sol-gel technique," *Langmuir*, 15:4328-4334.
Li et al., (2003) "Facilitation of $Ca^{2+}$-Dependent Exocytosis by Rac1-GTPase in Bovine Chromaffin," *Cells. J. Physiol.*, 550:431-445.
Li et al., (2008) "The Translocation of Fullerenic Nanoparticles into Lysosome via the Pathway of Clathrin-Mediated Endocytosis," *Nanotechnology*, 19:145102, 13 pp.
Li et al., (2008) *Molecular Pharmaceutics*, 5(4):496-504.
Lichstein et al., (1994) *J. Bacteriol.*, 47:231-238.
Lim et al., (1997) *J. Am. Chem. Soc.*, 119:4090-4091.
Lin et al., (2009) *Chem. Mater.*, 21:3979-3986.
Liong et al., (2008) "Multifunctional inorganic nanoparticles for imaging, targeting and drug delivery," *ACS Nano*, 2(5):889-896 [and supporting information attached].
Liong et al., (2009) "Antimicrobial Activity of Silver Nanocrystals Encapsulated in Mesoporous," *Advanced Materials*, 21:1684-1689.
Liong et al., (2009) "Mesostructured Multifunctional Nanoparticles for Imaging and Drug Delivery," *J. Mater. Chem.*, 19(35):6251-6257.
Litvak et al., (1999) "Inhibition of gastric cancer by camptothecin involves apoptosis and multiple cellular pathways," *Surgery*, 125(2):223-230.
Liu et al., (2002) "Self-Directed Assembly of Photoactive Hybrid Silicates Derived from an Azobenzene-Bridged Silsesquioxane," *J. Am. Chem. Soc.*, 124:14540-14541.
Liu et al., (2003) *Angew. Chem. Int. Ed., Engl.*, 42:1731-1734.
Liu et al., (2003) *Chem. Comm.*, 10:1144-1145.
Liu et al., (2004) *J. Nano Lett.*, 4:551-554.
Liu et al., (2009) "Preparation of spherical large particle MCM-41 with a braod particle size distribution by modofied pseudomorphic transformation," *Microporous and mesoporous materials*, 121:73-78.
Liu et al., (2011) *Biomaterials*, 32:1657-1668.
Lobo et al., (2007) "Paclitaxel Albumin-Bound Particles (Abraxane(TM)) in Combination with Bevacizumab with or without Gemcitabine: Early Experience at the University of Miami/Braman Family Breast Cancer Institute," *Biomed. Pharmacother.*, 61:531-533.
Loher et al., (2008) "Micro-organism-triggered release of silver nanoparticles from biodegradable oxide carriers allows preparation of self-sterilizing polymer surfaces," *Small*, 4(6):824-832.
Lok et al., (2006) "Proteomic analysis of the mode of antibacterial action of silver nanoparticles," *Journal of Proteome Research*, 5:916-924.
Lu et al., (1997) *Nature*, 389:364-368.
Lu et al., (2002) "Modifying the surface properties of superparamagnetic iron oxide nanoparticles through a sol-yel approach," *Nano Letter*, 2(3):183-186.
Lu et al., (2007) "Mesoporous Silica Nanoparticles for Cancer Therapy: Energy-Dependent Cellular Uptake and Delivery of Paclitaxel to Cancer Cells," *Nanobiotechnology*, 3:89-95.
Lu et al., (2008) "Light-Activated Nanoimpeller-Controlled Drug Release in Cancer Cells," *Small*, 4(4):421-426.
Lu et al., (2010) *Small*, 6:1794-1805.
Ludwig et al., (2006) *Cancer Res.*, 66:4808-4815.
Luo et al., (2000) *Nat. Biotechnol.*, 18:893-895.
Maeda et al., (2009) *Eur. J. Pharm. Biopharm.*, 71:409-419.
Maeda et al., (2010) *Bioconjugate Chem.*, 21:797-802.
Mal et al., (2003) "Photo-Switched Storage and Release of Guest Molecules in the Pore Void of Coumarin-Modified MCM-41," *Chem. Mater.*, 15(17):3385-3394.
Mao et al., (2005) *Pharm. Res.*, 22:2058-2068.
Masuda et al., (1992) *J. Clin. Oncol.*, 10:1225-12229.
McBain et al., (2007) *J. Mater. Chem.*, 17:2561-2565.
Medarova et al., (2007) "In Vivo Imaging of siRNA Delivery and Silencing in Tumors," *Nat. Med.*, 13(3):372-377 (Published online Feb. 25, 2007).
Meng et al., (2009) "A Predictive Toxicological Paradigm for the Safety Assessment of Nanomaterials," *ACS Nano*, 3:1620-1627.
Meng et al., (2010) "Autonomous in Vitro Anticancer Drug Release from Mesoporous Silica Nanoparticles by pH- Sensitive Nanovalves," *J. Am. Chem. Soc.*, 132:12690-12697.
Meng et al., (2010) "Engineered Design of Mesoporous Silica Nanoparticles to Deliver Doxorubicin and P-Glycoprotein siRNA to Overcome Drug Resistance in a Cancer Cell Line," *ACS Nano*, 4(8):4539-4550.
Meng et al., (2010) "Potent Angiogenesis Inhibition by the Particulate Form of Fullerene Derivatives," *American Chemical Society*, 4(5):2773-2783.
Meng et al., (2011) "Aspect Ratio Determines the Quantity of Mesoporous Silica Nanoparticle Uptake by a Small GTPase-Dependent Macropinocytosis Mechanism," *ACS Nano*, 5(6):4434-4447.
Meng et al., (2011) "Use of Size and a Copolymer Design Feature to Improve the Biodistribution and the Enhanced Permeability and Retention Effect of Doxorubicin Loaded Mesoporous Silica Nanoparticles in a Murine Xenograft Tumor Model," *ACS Nano*, 5(5):4131-4144.
Mercer et al., (2009) Virus Entry by Macropinocytosis, *Nat. Cell Biol.*, 11:510-520.
Mignot et al., (2001) "Distribution of s-layers on the surface of bacillus cereus strains: phylogenetic origin and ecological pressure," *Environ. Microbiol.*, 3(8):493-501.
Miljanić et al., (2006) *Org. Lett.*, 8(21):4835-4838.
Miller et al., (2004) *Invest. New Drugs*, 22:69-73.
Minko et al., (2000) *Pharm. Res.*, 17:505-517.
Minoofar et al., (2002) "Placement and characterization of pairs of luminescent molecules in spatially separated regions of nanostructured thin films," *J. Am. Chem. Soc.*, 124:14388-14396.
Minoofar et al., (2005) "Multiply doped nanostructured silicate sol-gel thin films: Spatial segregation of dopants, energy transfer, and distance measurements," *J. Am. Chem. Soc.*, 127:2656-2665.
Mitragotri et al., (2009) "J. Physical Approaches to Biomaterial Design," *Nat. Mater.*, 8:15-23.
Moazed et al., (2009) *Nature*, 457:413-420.
Moller et al., (2007) "Colloidal Suspensions of Nanometer-Sized Mesoporous Silica," *Adv. Funct. Mater.*, 17:605-612.
Muggia et al., (1996) "Camptothecin and Its Analogs," and attachments, *Ann. N.Y. Acad. Sci.*, 803:213-223, 124 pages.
Mulvaney, (1996) "Surface Plasmon Spectroscopy of Nanosized Metal Particles," *Langmuir*, 12:788-800.

(56) References Cited

OTHER PUBLICATIONS

Munoz et al., (2003) *Chem. Mater.*, 15(2):500-503.
Muro et al., (2008) "Control of Endothelial Targeting and Intracellular Delivery of Therapeutic Enzymes by Modulating the Size and Shape of ICAM-1-targeted Carriers," *Mol. Ther.*, 16:1450-1458.
Na et al., (2007) "Development of a $T_1$ Contrast Agent for Magnetic Resonance Imaging Using MnO Nanoparticles," *Angew. Chem., Int. Ed.*, 46:5397-5401 (Published online Mar. 13, 2007).
Nakamura et al., (2007) "Direct synthesis of monodispersed thiol-functionalized nanoporous silica spheres and their application to a colloidal crystal embedded with gold nanoparticles," *J Mater Chem*, 17:3726-3732.
Nakase et al., (2004) "Cellular Uptake of Arginine-Rich Peptides: Roles for Macropinocytosis and Actin Rearrangement," *Mol. Ther.*, 10:1011-1022.
Nel et al., (2009) "Understanding Biophysicochemical Interactions at the Nano-Bio Interface," *Nat. Mater.*, 8:543-557.
Neu et al., (2005) *J. Gene. Med.*, 7:992-1009.
Nguyen et al., (2006) "Construction of a pH-Driven Supramolecular Nanovalve," *Organic Letters*, 8(15):3363-3366.
Nie et al., (2007) *Annu. Rev. Biomed. Eng.*, 9:12.1-12.32.
Noguchi et al., (1998) *Cancer Sci.*, 89:307-314.
Nomura et al., (2007) *Am. J. Roentgenol.*, 189:1484-1488.
Ohsuna et al., (2005) "Characterization of Chiral Mesoporous Materials by Transmission Electron Microscopy," *Small*, 1:233-237.
Onishi et al., (2005) *Curr. Drug Discovery Technol.*, 2(3):169-183.
Osada et al., (1999) "Effect of Mechanical Strain on Gastric Cellular Migration and Proliferation During Mucosal Healing: Role of Rho Dependent and Rac Dependent Cytoskeletal Reorganisation," *Gut*, 45:508-515.
Paciotti et al., (2006) "Colloidal Gold Nanoparticles: A Novel Nanoparticle Platform for Developing Multifunctional Tumor-Targeted Drug Delivery Vectors," *Drug Dev Res*, 67:47-54.
Padilla De Jesús et al., (2002) *Bioconjug Chem.*, 13:453-461.
Pal et al., (2007) "Does the Antibacterial Activity of Silver Nanoparticles Depend on the Shape of the Nanoparticle? A Study of the Gram-Negative Bacterium *Escherichia coli*," *Applied and Environmental Microbiology*, 73 (6): 1712-1720.
Pantos et al., (2005) *Langmuir*, 21:7483-7490.
Paranjpe et al., (2004) "Tumor-targeted bioconjugate based deliver of camptothecin: design, synthesis and in vitro evaluation," *Journal of Controlled Release*, 100:275-292.
Park et al., (2004) "Ultra-Large-Scale Syntheses of Monodisperse Nanocrystals," *Nat. Mater.*, 3:891-895.
Park et al., (2008) *Int. J. Pharm.*, 359:280-284.
Pasqua et al., (2007) "Preparation of bifunctional hybrid mesoporous silica potentially useful for drug targeting," *Microporous and Mesoporous Materials*, 103:166-173 (Published online Feb. 3, 2007).
Patel et al., (2008) Enyzme-Responsive Snap-Top Covered Silica Nanocontainers, *J. Am. Chem. Soc.*, published on web, 130:2382-2383.
Patil et al., (2009) *Biomaterials*, 31:358-365.
Pearse et al., (1987) *Annu. Rev. Biophys. Biophys. Chem.*, 16:49-68.
Peng et al., (2009) *Bioconjugate Chem.*, 20:340-346.
Perrault et al., (2009) *Nano Lett.*, 9:1909-1915.
Petersen et al., (2002) *Bioconjugate Chem.*, 13:845-854.
Phillips et al., (2008) "Rapid and Efficient Identification of Bacteria Using Gold-Nanoparticle-Poly(para-phenyleneethynylene) Constructs," *Angew. Chem., Int. Ed.*, 47:2590-2594.
Portney et al., (2006) *Anal. Bioanal. Chem.*, 386:620-630.
Radu et al., (2004) "A Polyamidoamine Dendrimer-Capped Mesoporous Silica Nanosphere-Based Gene Transfection Reagent," *J. Am. Chem. Soc.*, 126(41):13216-13217.
Radu et al., (2004) "A Polyamidoamine Dendrimer-Capped Mesoporous Silica Nanosphere-Based Gene Transfection Reagent," *J. Am. Chem. Soc.*, 126:13216-13217 [and supporting information attached].
Radu et al., (2005) "Fine-tuning the degree of organic functionalization of mesoporous silica nanosphere materials via an interfacially designed co-condensation method," *Chem. Commun.*, 1264-1266.
Ridley et al., (1992) "The Small GTP-binding Protein Rae Regulates Growth Factor-Induced Membrane Ruffling," *Cell*, 70:401-410.
Roiter et al., (2008) "Interaction of Nanoparticles with Liquid Membrane," *Nano Lett.*, 8:941-944.
Roma et al. (2000) *Hepatology*, 32(6): 1342-1356.
Rostovtsev et al., (2002) *Angew. Chem., Int. Ed.*, 41:2596-2599.
Ruenraroengsak et al., (2010) *J. Controlled Release*, 141:265-276.
Saad et al., (2008) *Nanomedicine*, 3:761-776.
Saha et al., (2007) "Nanovalves," *Adv. Funct. Mater.*, 17:685-693.
Sahay et al., (2010) "Endocytosis of Nanomedicines," *J. Control. Release*, 145:182-195.
Samson et al., (1979) *J. Pharmacal. Exp. Ther.*, 208(3):411-417.
Sandgren et al., (2010) "A Differential Role for Macropinocytosis in Mediating Entry of the Two Forms of Vaccinia Virus into Dendritic Cells," *PLoS Pathog.*, 6(4):e1000866, 16 pages.
Santra et al., (2004) *Chem. Commun.*, 2810-2811.
Santra et al., (2005) "Folate Conjugated Fluorescent Silica Nanoparticles for Labeling Neoplastic Cells," *Journal of Nanoscience and Nanotechnology*, 5(6):899-904.
Schiestel et al., (2004) "Controlled Surface Functionalization of Silica Nanospheres by Covalent Conjugation Reactions and Preparation of High Density Streptavidin Nanoparticles," *Journal of Nanoscience and Nanotechnology*,4(5):504-511.
Schrijvers et al., (2004) "Flow Cytometric Evaluation of a Model for Phagocytosis of Cells Undergoing Apoptosis," *J. Immunol. Methods*, 287:101-108.
Scott et al., (1993) *Pharm. Res.*, 10(3):335-342.
Sheldon et al., (2009) "Active Involvement of Robo1 and Robo4 in Filopodia Formation and Endothelial Cell Motility Mediated via WASP and Other Actin Nucleation-Promoting Factors," *FASEB J.*, 23:513-522.
Shidhaye et al., (2008) "Nanogel Engineered Polymeric Micelles for Drug Delivery," *Current Drug Therapy*, 3(3):209-217.
Shim et al., (2009) *J. Control. Release.*, 133:206-213.
Shrivastava et al., (2007) "Characterization of enhanced antibacterial effects of novel silver nanoparticles," *Nanotechnology*, 18:225103(9pp).
Sierocki et al., (2006) *J. Phys. Chem. B*, 110:24390-24398.
Slowing et al., (2007) "Mesoporous Silica Nanoparticles for Drug Delivery and Biosensing Applications" *Adv. Funct. Mater.*, 17:1225-1236.
Slowing et al., (2008) "Mesoporous silica nanoparticles as controlled release drug delivery and gene transfection carriers," *Adv. Drug Deliv. Rev.*, 60:1278-1288.
Slowing et al., (2009) "Mesoporous Silica Nanoparticles for Reducing Hemolytic Activity Towards Mammalian Red Blood Cells," *Small*, 5:57-62.
Sonawane et al., (2002) *J. Biol. Chem.*, 277:5506-5513.
Sondi et al., (2004) "Silver nanoparticles as antimicrobial agent: a case study on *E. coli* as a model for Gram-negative bacteria," *Journal of Colloid and Interface Science*, 275:177-182.
Soppimath et al., (2007) "Multifunctional Core/Shell Nanoparticles Self-Assembled from pH-Induced Thermosensitive Polymers for Targeted Intracellular Anticancer Drug Delivery," *Adv. Funct. Mater.*, 17:355-362 (Published online Jan. 9, 2007).
Souris et al., (2010) *Biomaterials*, 31:5564-5574.
Stein et al., (2000) "Hybrid Inorganic-Organic Mesoporous Silicates-Nanoscopic Reactors Coming of Age," *Adv. Mater.*, 12(19):1403-1419.
Sudimack et al., (2000) "Targeted Drug Delivery Via the Folate Receptor," *Adv. Drug Delivery Rev.*, 41:147-162.
Sugahara et al., (2010) *Science*, 328:1031-1035.
Sun et al., (2004) "Monodisperse $MFe_2O_4$ (M=Fe, Co, Mn) Nanoparticles," *J. Am. Chem. Soc.*, 126(1):273-279.
Suzuki et al., (1981) *J. Natl. Cancer Inst.*, 67:663-669.
Szakacs et al., (2006) *Nat. Rev. Drug Discov.*, 5:219-234.
Takiguchi et al., (1994) *Gan to Kagaku Ryoho*, 21(5):705-708.
Tang et al., (2003) *Biomaterials*, 24:2351-2362.
Tarimala et al., (2006) "New Approach to antibacterial treatment of cotton fabric with silver nanoparticle-doped silica using sol-gel process," *J. Appl. Poly. Sci.*, 101:2938-2943.

(56) References Cited

OTHER PUBLICATIONS

Taylor et al., (2008) "Mesoporous Silica Nanospheres as Highly Efficient MRI Contrast Agents," *J. Am. Chern. Soc.*, 130:2154-2155.
Thery et al., (2006) "Anisotropy of Cell Adhesive Microenvironment Governs Cell Internal Organization and Orientation of Polarity," *Proc. Natl. Acad. Sci. U.S.A.*, 103:19771-19776.
Thiel et al., (2007) "Antibacterial Properties of Silver-Doped Titania," *Small*, 3(5):799803.
Thierry et al., (2008) *Langmuir*, 24:8143-8150.
Tietze et al., (2006) *Angew. Chem. Int. Ed.*, 45:6574-6577.
Torchilin et al., (2011) *Adv. Drug Deliver. Rev.*, 63:131-135.
Torney et al., (2007) *Nat. Nanotechnol.*, 2:295-300.
Tornoe et al., (2002) *J. Org. Chem.*, 67:3057-3064.
Trewyn et al., (2004) "Morphological Control of Room-Temperature Ionic Liquid Templated Mesoporous Silica Nanoparticles for Controlled Release of Antibacterial Agents," *Nano Letter*, 4(11):2139-2143.
Trewyn et al., (2007) "Synthesis and Functionalization of a Mesoporous Silica Nanoparticle Based on the Sol-Gel Process and Applications in Controlled Release," *Accounts of Chemical Research*, 40(9):846-853.
Trewyn et al., (2008) "Biocompatible mesoporous silica nanoparticles with different morphologies for animal cell membrane penetration," *Chem. Engineering Journal*, 137:23-29 [published on Oct. 5, 2007].
Tsai et al., (2008) "High-Contrast Paramagnetic Fluorescent Mesoporous Silica Nanrods as a Multifunctional Cell-Imaging Probe," *Small*, 4(2):186-191 (Published online Jan. 18, 2008).
Ueda et al., (2008) Activation of the Small GTPase Rac 1 by a Specific Guanine-Nucleotide-Exchange Factor Suffices to Induce Glucose Uptake into Skeletal-Muscle Cells, *Biol. Cell.*, 100:645-657.
Ung et al., (1998) "Controlled Method for Silica Coating of Silver Colloids. Influence of Coating on the Rate of Chemical Reactions," *Langmuir*, 14:3740-3748.
Urban-Klein et al., (2005) *Gene Ther.*, 12:461-466.
Vallet-Regi et al., (2001) *Chem. Mater.*, 13:308-311.
van Vlerken et al., (2007) *Cancer Res.*, 67:4843-4850.
Veiseh et al., (2009) *Biomaterials*, 30:649-657.
Verbaan et al., (2004)*J. Gene Med.*, 6:64-75.
Wagner et al., (Oct. 2006) *Nat. Biotechnol.*, 24(10):1211-1217.
Wang et al., (2002) "Gene Expression Profiling in Multidrug Resistant Kb Cells Using Cdna Microarrays," *Chinese J. Cancer Res.*, 14(1):5-10.
Wang et al., (2007) "Fluorescent Nanoparticles for Multiplexed Bacteria Monitoring," *Bioconjugate Chem.*, 18:297-301 (Published online Mar. 7, 2007).
Wang (2009) "Ordered mesoporous materials for drug delivery," *Microporous and Mesoporous Materials, Department of Chemical Engineering*, 117:pp. 1-9 (Published online, Jul. 9, 2008).
Wani et al., (1971) *J. Am. Chem. Soc.*, 93:2325-2327.
Weh et al., (2002) *J. Microporous Mesoporous Mater.*, 54:15-26.
Wessing et al., (1993) *J. Comp. Physiol.*, 163:452-462.
West et al., (1989) "Distinct Endocytotic Pathways in Epidermal Growth Factor-Stimulated Human Carcinoma A431 Cells," *J. Cell Biol.*, 109:2731-2739.
Woodroofe et al., (2003) *J. Am. Chem. Soc.*, 125:11458-11459.
Word Counts of Abstract (AN12/841331), one page.
Wu et al., (2002) "Immunofluorescent Labeling of Cancer Marker Her2 and Other Cellular Targets with Semiconductor Quantum Dots," *Nat. Biotechnol.*, 21:41-46.
Wu et al., (2007) *J. Pharm. Pharmaceut. Sci.*, 10:350-357.
Wu et al., (2008) "Multifunctional Mesoporous Silica Nanoparticles for Intracellular Labeling and Animal Magnetic Resonance Imaging Studies," *Chem Bio Chem.*, 9:53-57 (Published online Nov. 12, 2007).
Xia et al., (2006) "Comparison of the Abilities of Ambient and Manufactured Nanoparticles to Induce Cellular Toxicity According to an Oxidative Stress Paradigm," *Nano Lett.*, 6(8):1794-1807.

Xia et al., (2008) "Comparison of the Mechanism of Toxicity of Zinc Oxide and Cerium Oxide Nanoparticles Based on Dissolution and Oxidative Stress Properties," *ACS Nano*, 2(10):2121-2134.
Xia et al., (2008) "Cationic Polystyrene Nanosphere Toxicity Depends on Cell-Specific Endocytic and Mitochondrial Injury Pathways," *ACS Nano*, 2(1):85-96.
Xia et al., (2009) "Polyethyleneimine Coating Enhances the Cellular Uptake of Mesoporous Silica Nanoparticles and Allows Safe Delivery of siRNA and DNA Constructs," *ACS Nano*, 3(10):3273-3286.
Xing et al., (2005) *J. Nanosci. Nanotechnol.*, 5:1688-1693.
Xu et al., (2003) "Room-Temperature Preparation and Characterization of Poly(ethylene glycol)-Coated Silica Nanoparticles for Biomedical Applications," *J. Biomed. Mater. Res., Part A* 66A:870-879.
Yager et al., (2006) "Novel photo-switching using azobenzene functional materials," *Journal of Photochemistry and Photobiology, A: Chemistry*, 182:250-261.
Yagmurca et al., (2004) *Clinica. Chimica. Acta.*, 348:27-34.
Yang et al., (2006) "On the Origin of Helical Mesostructures," *J. Am. Chem. Soc.*, 128:10460-10466.
Yang et al., (2007) "Siliceous Nanopods from a Compromised Dual-Templating Approach," *Angew. Chem. Int. Ed. Engl.*, 46:8579-8582.
Yezhelyev et al., (2008) *J. Am. Chem. Soc.*, 130(28):9006-9012.
Yi et al., (2006) "Nanoparticle Architectures Templated by $SiO_2$/$Fe_2O_3$ Nanocomposites," *Chem. Mater.*, 18(3):614-619.
Ying et al., (1999) "Synthesis and Applications of Supramolecular-Templated Mesoporous Materials," *Angew. Chem., Int. Ed*, 38:56-77.
Yu et al., (2004) "Synthesis of Monodisperse Iron Oxide Nanocrystals by Thermal Decomposition of Iron Carboxylate Salts," *Chem. Commun.*, 2306-2307.
Zhang et al., (2007) "Synthesis of Poly(ethylene glycol) (PEG)-Grafted Colloidal Silica Particles with Improved Stability in Aqueous Solvents," *J. Colloid Interface Sci.*, 310:446-455 (Feb. 14, 2007).
Zhang et al., (2008) "Fabrication of a Magnetic Helical Mesostructured Silica Rod," *Nanotechnology*, 19:435608.
Zhang et al., (2010) *Biomaterials*, 31:952-963.
Zhang et al., (2011) *ACS Nano*, 5(4):2756-2769.
Zhao et al., (2004) "In situ formation of silver nanoparticles inside pore channels of ordered mesoporous silica," *Mater. Lett.*, 58:2152-2156.
Zhou et al., (Sep. 2006) "Zirconium Phosphonate-Modified Porous Silicon for Highly Specific Capture of Phosphopeptides and MALDI-TOF MS Analysis," *Journal of Proteome Research*, 5:2431-2437.
Zhu et al., (2004) *Biotechnol. Appl. Biochem.*, 39:179-187.
U.S. Final Office Action, dated Aug. 29, 2016, issued in U.S. Appl. No. 12/746,375.
U.S. Office Action, dated Mar. 31, 2017, issued in U.S. Appl. No. 12/746,375.
U.S. Office Action (Before the Patent Trial and Appeal Board, Decision on Appeal), dated Aug. 31, 2016, issued in U.S. Appl. No. 12/812,359.
U.S. Final Office Action, dated Aug. 18, 2016, issued in U.S. Appl. No. 12/841,331.
U.S. Office Action, dated Dec. 2, 2016, issued in U.S. Appl. No. 13/140,714.
U.S. Final Office Action, dated Mar. 7, 2017, issued in U.S. Appl. No. 13/428,830.
U.S. Office Action (Restriction Requirement), dated Feb. 3, 2017, issued in U.S. Appl. No. 14/772,740.
European Extended Search Report dated Jul. 27, 2016 issued in Application No. EP 14 760 467.2.
Ashley et al., (2011) "The targeted delivery of multicomponent cargos to cancer cells by nanoporous particle-supported lipid bilayers," *Nature Materials*, 10(5):389-397.
Berry et al. (2003) "Functionalization of magnetic nanoparticles for applications in biomedicine," *J. Phys. D: Appl. Phys.*, R198-206, 10pp.

(56) References Cited

OTHER PUBLICATIONS

Fritze et al., (2006) "Remote loading of doxorubicin into liposomes driven by transmembrane phosphate gradient," *Biochimica Et Biophysica Acta (BBA)—Biomembranes*, Elsevier, Amsterdam, NL, 1758(10):1633-1640.

Liu et al., (2009) "Porous Nanoparticle Supported Lipid Bilayers (Protocells) as Delivery Vehicles," *Journal of the American Chemical Society*, 131(4):1354-1355.

Mock et al., (1990) "A Cucurbituril-based Molecular Switch," *Journal of the Chemical Society*, Chemical Communications, 21:1509-1511.

Yiu et al. (2007) "A triple-layer design for polyethyleneimine-coated, nanostructured magnetic particles and their use in DNA binding and transfection," *Nanotechnology*, 18:1-6.

Guiotto et al., (2004) "Synthesis, Characterization, and Preliminary in Vivo Tests of New Poly(ethylene glycol) Conjugates of the Antitumor Agent 10-Amino-7-ethylcamptothecin" J. Med. Chem., 47(5):1280-1289 [Abstract—2pages].

U.S. Notice of Allowance, dated Jan. 17, 2018, issued in U.S. Appl. No. 12/746,375.

U.S. Notice of Allowance (Corrected), dated Feb. 8, 2018, issued in U.S. Appl. No. 12/746,375.

U.S. Office Action, dated Oct. 25, 2017, issued in U.S. Appl. No. 15/288,322.

U.S. Office Action, dated Nov. 22, 2017, issued in U.S. Appl. No. 12/841,331.

U.S. Office Action, dated May 15, 2018, issued in U.S. Appl. No. 15/698,486.

Slowing et al., (2006) "Effect of Surface Functionalization of MCM-41-Type Mesoporous Silica Nanoparticles on the Endocytosis by Human Cancer Cells Supporting Information," *J. Am. Chem. Soc.*, 11 pages.

Yin et al., (2015) "How does fluorescent labeling affect the binding kinetics of proteins with intact cells?," *Biosens Bioelectron.*, 66: 412-416 [HHS Public Access—Author manuscript—11 pages].

\* cited by examiner

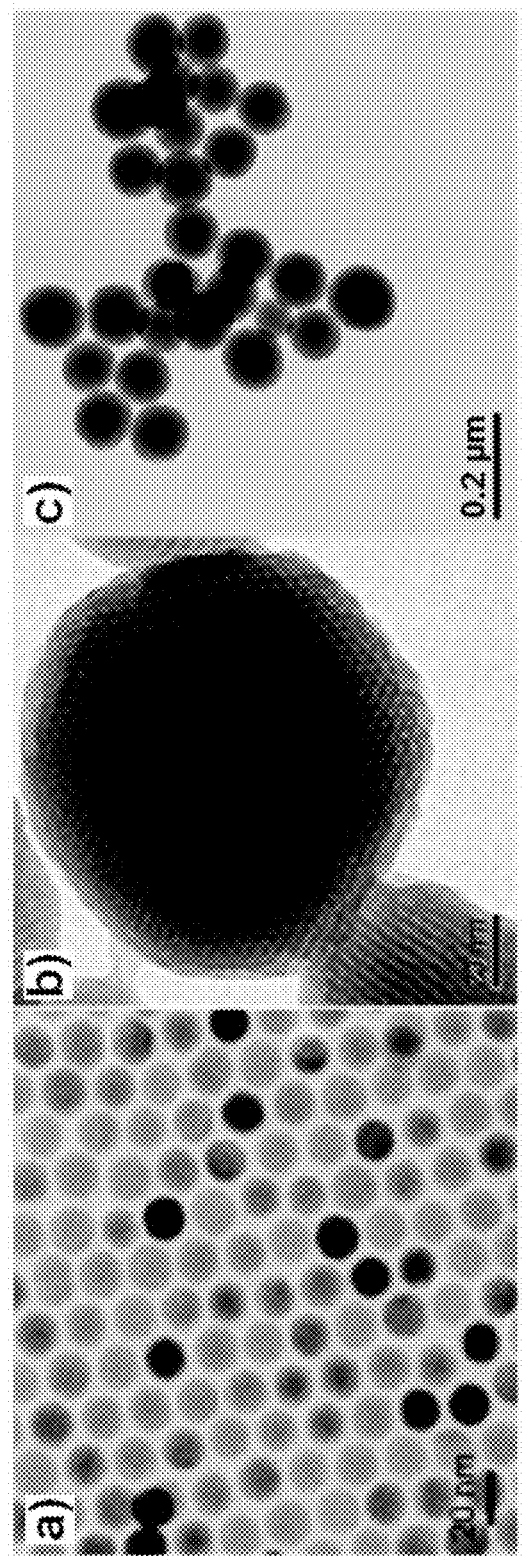

METHOD OF CONTROLLED DELIVERY USING SUB-MICRON-SCALE MACHINES

CROSS-REFERENCE OF RELATED APPLICATION

This application claims priority to U.S. Provisional Application No. 61/507,737 filed Jul. 14, 2011, the entire contents of which are hereby incorporated by reference.

This invention was made with Government support under Grant No. 0809384, awarded by the National Science Foundation. The Government has certain rights in this invention.

BACKGROUND

1. Field of Invention

The field of the currently claimed embodiments of this invention relates to methods of controlled delivery of substances within a body, and more particularly to methods of controlled delivery of substances within a body using sub-micron, heat-actuated containment vessels.

2. Discussion of Related Art

Mesoporous silica nanoparticles (MSNs) have attracted widespread research interest as functional materials.[1-7] They are endocytosed by cells,[1] are nontoxic,[2] and can be used to deliver drugs.[3] Recently, an amazing array of methods for controlling pores to trap and release cargo has been developed. These range from coatings on particles, to intricate nanovalves that control the pore openings using methods of light,[4] pH,[5] or redox[6] for activation. For therapeutic applications, an external and noninvasive method of actuation is preferable for control of therapeutic effects. Light control has been demonstrated, but its practical applicability is limited due to shallow tissue penetration for photodynamic therapies. Nanovalves based on changes in pH are self-opening, but cannot be controlled by an external stimulus. Therefore, there remains a need for improved methods of controlled delivery of substances within a body.

SUMMARY

A method for controlled delivery of a substance into a body according to some embodiments of the current invention includes administering a plurality of containment vessels into the body, in which each of the plurality of containment vessels includes a quantity of the substance loaded therein prior to the administering; and providing a time-varying magnetic field such that the plurality of containment vessels are exposed thereto to cause a release of at least a portion of the substance from the plurality of containment vessels. Each of the plurality of containment vessels has an average outer diameter less than about 1 µm.

A containment vessel for controlled delivery of a substance into a body according to some embodiments of the current invention includes a vessel body defining a containment space and a plurality of pores that allow the substance to be loaded into and released from the containment space, a plurality of heat-operable valve assemblies attached to the vessel body, and a magnetic substructure adapted to provide inductive heating when exposed to a time-varying magnetic field to cause the heat-operable valves to release the at least a portion of the substance. The vessel body consists essentially silica, the plurality of heat-operable valve assemblies include adamantylethyl trichlorosilane attached to the vessel body and alpha-cyclodextrin as caps, and the caps are at least one of movable or removable in response to the inductive heating.

A composition for controlled delivery of a substance into a body according to some embodiments of the current invention includes a plurality of containment vessels, and a quantity of the substance loaded into each of the plurality of containment vessels. Each of the plurality of containment vessels includes a vessel body defining a containment space and a plurality of pores that allow the substance to be loaded into and released from the containment space, a plurality of heat-operable valve assemblies attached to the vessel body, and a magnetic substructure adapted to provide inductive heating when exposed to a time-varying magnetic field to cause the heat-operable valves to release the at least a portion of the substance. The vessel body consists essentially silica, the plurality of heat-operable valve assemblies include adamantylethyl trichlorosilane attached to the vessel body and alpha-cyclodextrin as caps, and the caps are at least one of movable or removable in response to the inductive heating.

BRIEF DESCRIPTION OF THE DRAWINGS

Further objectives and advantages will become apparent from a consideration of the description, drawings, and examples.

FIG. 2A-2C show electron micrographs of zinc-doped iron oxide (image a, ZnNCs) and ZnNCs encapsulated within mesoporous silica (images b-c).

DETAILED DESCRIPTION

Figure 1:
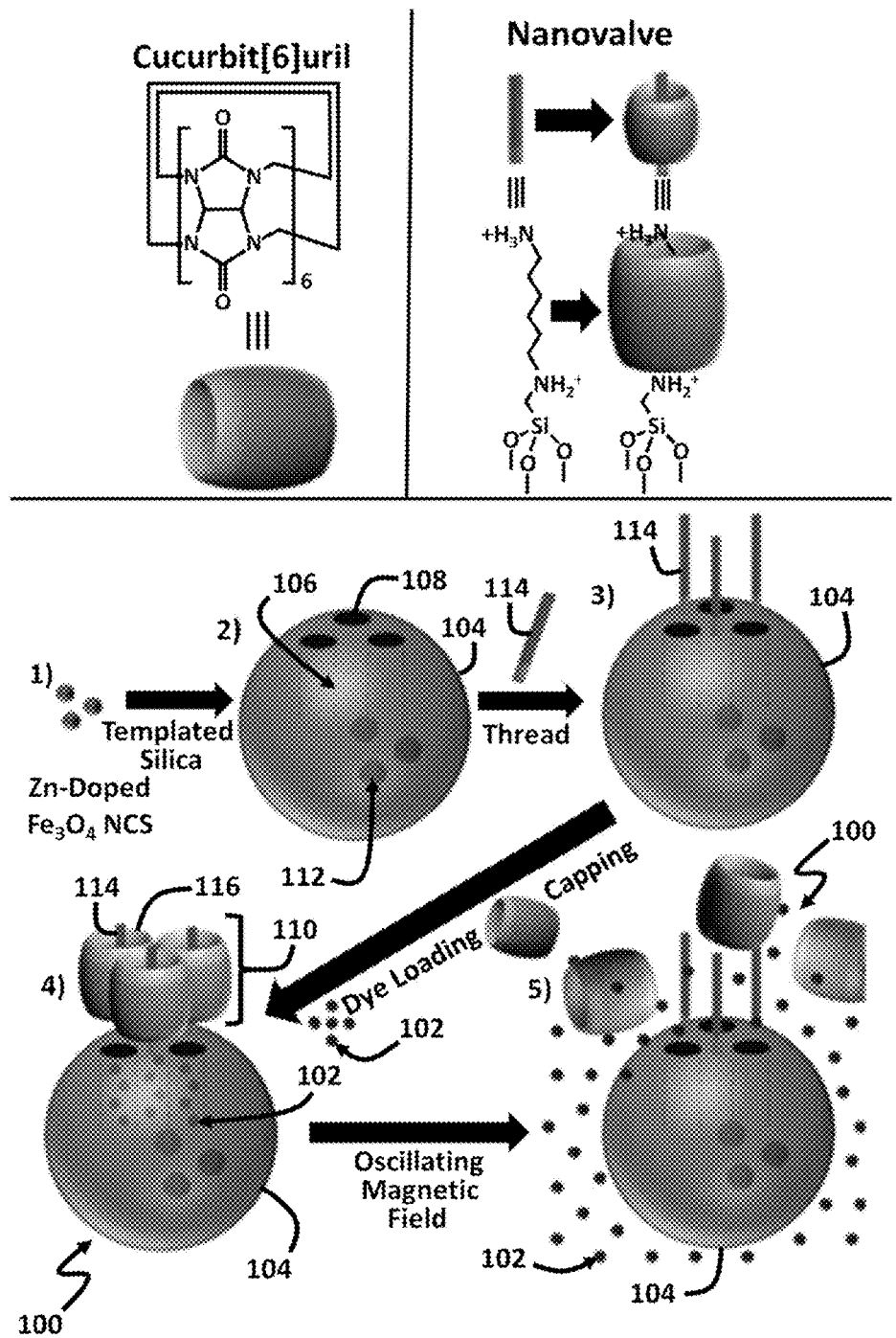
FIG. 1 provides a schematic illustration of nanoparticles, machines and assembly according to an embodiment of the current invention. ZnNCs (1) synthetically positioned at the core of the mesoporous silica nanoparticles (2). The base of the molecular machine then attached to the nanoparticle surface (3). Drug loaded into the particle and capped (4) to complete the system. Release can be realized using remote heating via the introduction of an oscillating magnetic field (5). The particles and machines are not drawn to scale.
Figure 3A:
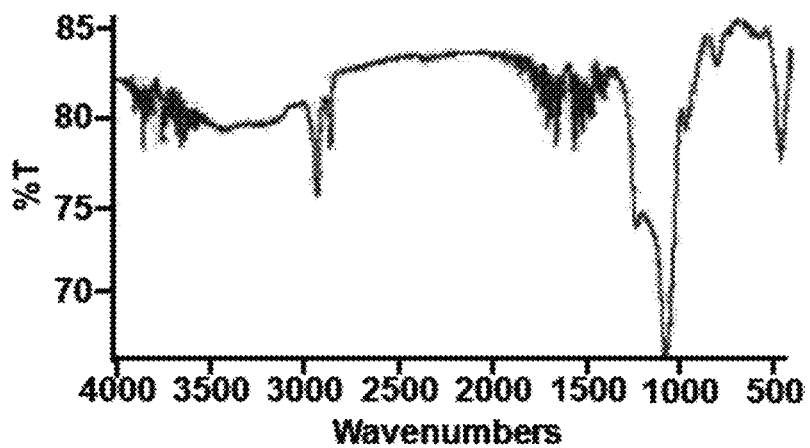
FIGS. 3A-3D show the IR spectra of the MCM-41 nanoparticles from KBr pellets (a) before and (b) after extraction. The loss of the C—H peak at ~2900 $cm^{-1}$ indicates the removal of the surfactant. The XRD of the MCM-41 nanoparticles (c) before, and (d) after extraction. The retention of the spectrum indicates that the mesostructure of the MCM-41 nanoparticles is maintained after the extraction. A d-spacing of 4 nm indicates that the pores are approximately 2 nm in diameter. The magnetic nanoparticles' mesoporous template is generated by the CTAB micelle structure with condensation of TEOS around the surfactant. Removal of the template was confirmed using IR (Figure S1b). Retention of the porous structure is confirmed by XRD. Particle size determination is performed using dynamic light scattering (DLS).
Figure 3B:
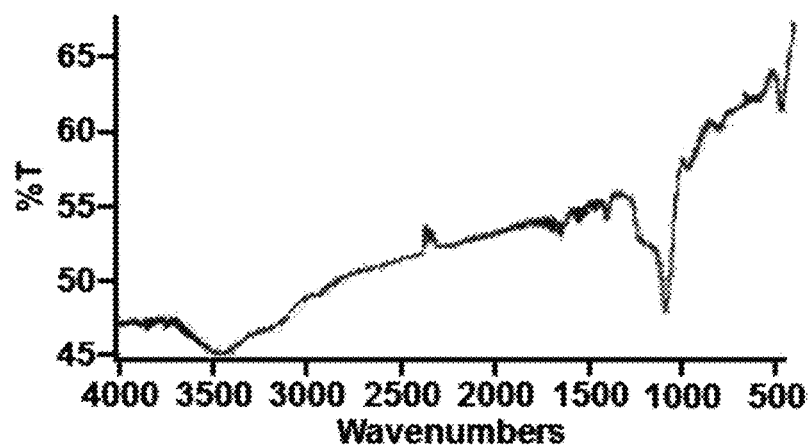
Figure 3C:
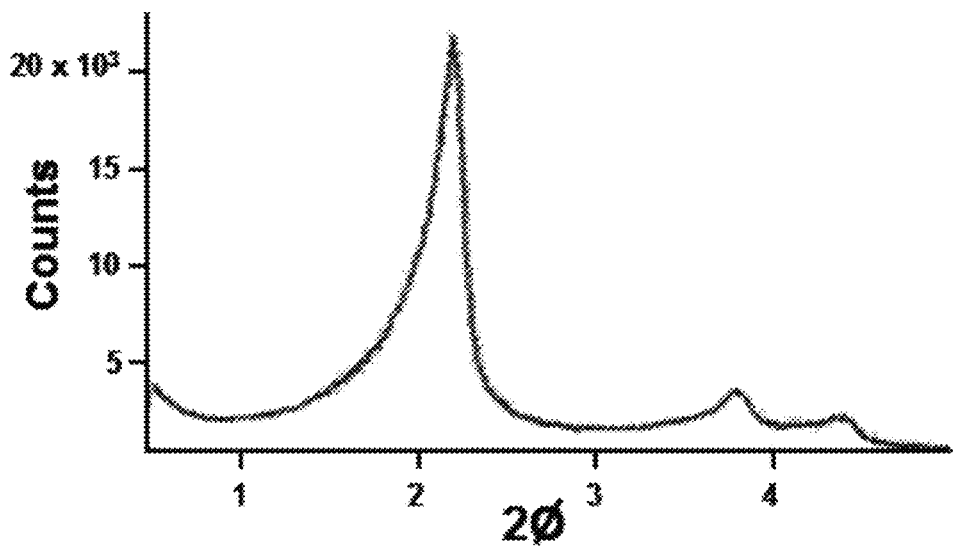
Figure 3D:
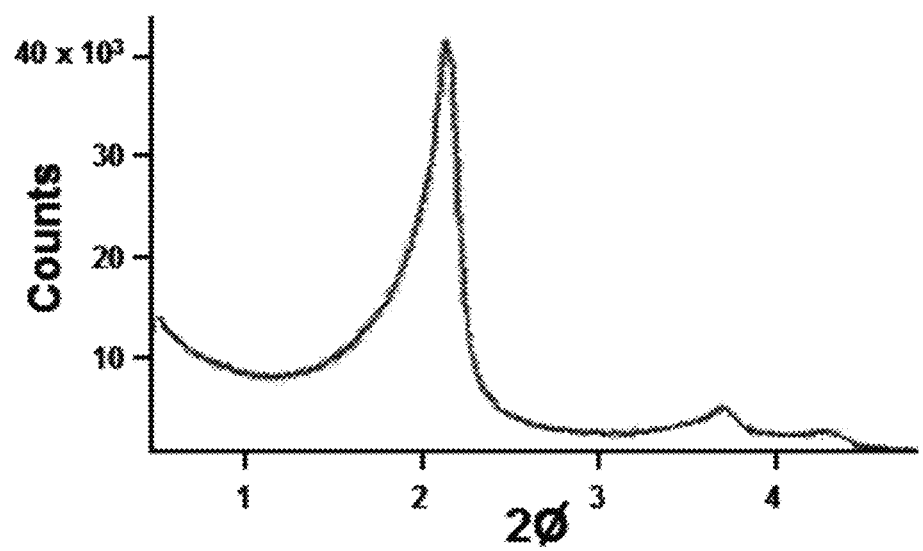

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The lack of an effective, external control for in vivo applications can be overcome according to some embodiments of the current invention by a new class of materials driven by a magnetic core. Magnetic nanocrystals (NCs) are of importance in biomedical applications, as they can be used for both therapeutics and imaging. The usefulness of magnetic materials for inducing hyperthermic effects when placed in an oscillating magnetic field[7] and for T2 MRI contrast[8] make magnetic NCs theranostic. Among those developed, zinc-doped iron oxide nanocrystals (ZnNCs)[9] improve upon existing materials by offering a fourfold increase in hyperthermic effects, and a roughly tenfold increase in MRI contrast when compared to undoped iron oxide NCs.

Some embodiments of the current invention combine advantages of mechanized silica (MSNs with nanovalves) with those of zinc-doped iron oxide, for example, to create a new generation of drug delivery systems responsive to heat activation. To this effect, a nanovalve is provided that is not self-opening in biological systems, thermally stable at room temperature, and that can be operated under heating.

When this type of nanovalve is attached to the surface of a mesoporous particle, an increase in temperature causes the valve to open, allowing materials contained within to diffuse out. If the nanoparticles contain ZnNCs, then application of an oscillating magnetic field will induce local heating, which can result in the same drug release effect. This novel approach to drug delivery allows cargo containment within the nanoparticle at body temperature, but upon local heating generated by the ZnNCs, controlled release of a therapeutic agent to induce apoptosis is made possible.

Accordingly, an embodiment of the current invention is directed to a method for controlled delivery of a substance into a body that includes administering a plurality of containment vessels into the body in which each of the plurality of containment vessels has a quantity of the substance loaded therein prior to said administering, and providing a time-varying magnetic field such that the plurality of containment vessels are exposed thereto to cause a release of at least a portion of the substance from the plurality of containment vessels.

The term "body" is intended to have a broad definition that can include living organisms as well as inanimate objects. The term "body" includes, but is not limited to, an animal or a human body. It can also include in vitro lab specimens, liquid solutions and/or liquid dispersions, for example. It can also include plants, plant portions or plant cells, and/or microbial organisms, for example.

The term "substance" is intended to have a broad meaning that can include elemental and/or molecular compositions. The molecular compositions can include inorganic and/or organic compositions, which can include small molecule and/or large molecule organic compositions. Generally, any composition of matter that can be loaded into and at least partially released from the containment vessels are intended to be included within the broad definition of the term "substance". The term "cargo" is also used for a quantity of the substance that is loaded into one or more containment vessels.

Each of the plurality of containment vessels has an average outer diameter less than about 1 µm. In some embodiments, each of the plurality of containment vessels administered has an average outer diameter less than about 300 nm. In some embodiments, each of the plurality of containment vessels administered has an average outer diameter less than about 200 nm and greater than about 50 nm. Containment vessels that have an average outer diameter less than about 300 nm can be suitable for applications in which it is desirable for the to enter into living cells, for example. Containment vessels that have an average outer diameter less than about 200 nm can be more suitable for some applications in which it is desirable for the to enter into living cells, for example. Containment vessels that have an average outer diameter greater than about 50 nm can be suitable for containing a useful cargo size, for some applications. In some embodiments, the containment vessels can also be referred to as nanoparticles or nanomachines.

In some embodiments, each of the plurality of containment vessels administered has a longitudinal dimension that is longer than corresponding two mutually orthogonal dimensions. In some embodiments, a ratio of the longitudinal dimension to at least one of the two mutually orthogonal dimensions is at least 2. In some embodiments, each of the plurality of containment vessels is substantially rod-shaped. Such non-spherical or rod-shaped containment vessels can provide an enhanced ability to enter into living cells, for example, in some applications. (See also U.S. patent application Ser. No. 13/428,830 assigned to the same assignee as the current application, the entire content of which is incorporated herein by reference.)

In some embodiments, the body can be a living organism that has cancer cells, the substance can be, or at least include, an anticancer drug, and the providing the time-varying magnetic field to which the plurality of containment vessels are exposed can be performed after the plurality of containment vessels have entered into at least some of the cancer cells within the living organism such that the anticancer drug is released within the cancer cells for cancer treatment. In some embodiments, the living organism can be a human, and the anticancer drug can be doxorubicin, for example. However, the broad concepts of the current invention are not limited to these examples. More generally, in some embodiments, the substance can include at least one of a cosmetic, a therapeutic, a nutritional, and/or a diagnostic agent, for example. In some embodiments, the plurality of containment vessels can be made of biocompatible materials.

FIG. 1 is a schematic illustration that is useful to help describe some embodiments of methods for controlled delivery of a substance into a body as well as embodiments of novel containment vessels. Methods according to some embodiment can, but are not limited to, using the novel containment vessels described in the present specification.

In FIG. 1, containment vessel 100 for controlled delivery of a substance 102 into a body (not shown) includes a vessel body 104 defining a containment space 106 and a plurality of pores 108 that allow the substance 102 to be loaded into and released from the containment space 106. In the figure only one portion 106 of the containment space and its corresponding pore 108 is labeled as an example, although the figure illustrates three. However, in actually containment vessels 100, there can be a large number of pores. The containment vessel 100 also includes a plurality of heat-operable valve assemblies 110 are attached to the vessel body 104, and a magnetic substructure 112 adapted to provide inductive heating when exposed to a time-varying magnetic field to cause the heat-operable valves 110 to release at least a portion of the cargo. In an embodiment of the current invention, the vessel body 104 is silica, such as a mesoporous silica nanoparticle. In this embodiment, the plurality of heat-operable valve assemblies 110 each includes adamantylethyl trichlorosilane 114 attached to the vessel body 104 and alpha-cyclodextrin 116 as a cap. The caps are at least one of movable or removable in response to the inductive heating. (See also U.S. patent application Ser. No. 12/841,331 assigned to the same assignee as the current application, the entire content of which is incorporated herein by reference.) Some broad concepts of the current invention are intended to include thermosensitive caps more generally. For example, a thermo-sensitive polymer can be used according to some embodiments of the current invention. An azobenzene stalk with a cyclodextrin cap is thermo-sensitive. This can also be used as another embodiment of a valve assembly. In some embodiments, a valve that has a temperature sensitive binding constant, i.e., binding decreases with increasing temperature, can be used.

The magnetic substructure according to an embodiment of the current invention can include a plurality of super paramagnetic nanoparticles 112 in thermal contact with the vessel body 102. For example, the plurality of super paramagnetic nanoparticles 112 can be embedded within the silica of the vessel body 102, for example during the process of producing the vessel body 102. However, the concepts of the current invention are not limited to that particular example. In some embodiments, the plurality of super paramagnetic nanoparticles 112 can be zinc-doped iron oxide nanocrystals.

In some embodiments, the containment vessel 100 can further include a coating (not shown) to enhance dispersion within a fluid medium substantially without aggregation. In some embodiments, the containment vessel 100 can further include a coating to enhance uptake by said cancer cells preferentially over healthy cells instead of or in addition to the previously mentioned coating. (See also U.S. patent application Ser. No. 12/746,375 assigned to the same assignee as the current application, the entire content of which is incorporated herein by reference.)

In some further embodiments of the current invention, a composition for controlled delivery of a substance into a body can include a plurality of containment vessels, such as containment vessel 100, and a quantity of the substance loaded into each of the plurality of containment vessels. For example, a composition according to an embodiment of the current invention can include, but is not limited to, a plurality of containment vessels loaded with cargo dispersed in a suitable liquid.

In the example of FIG. 1, zinc-doped iron oxide nanoparticles at step 1) are provided and/or produced. Steps 2) to 4) show schematically the further steps of producing and loading the containment vessel 100. In this example, the cargo is dye molecules; however, the general concepts of the current invention are not limited to this example. In practice, the containment vessels, which could be, but are not limited to, the type of containment vessel 100 are administered to the body. This could be administering a plurality of containment vessels which loaded with anticancer drug as cargo to a cancer patient, for example. Once a sufficient number of the containment vessels have reached and entered into cancer cells in the patient, an oscillating magnetic field can be applied. This magnetic field will penetrate the patient without harm but will generate heat within the containment vessels due to the interactions with the magnetic nanoparticles. This causes the caps 116 to move or to be removed due to the heat generated to allow at least some of the cargo to be released from the containment vessels. This can be, for example, the release of anticancer drug. This can thus help to deliver more of the anticancer drug to cancer cells while decreasing side effects to healthy cells. In addition, the heat generated in the containment vessels can have a combined effect along with the anticancer drug to further enhance selective destruction of cancer cells. Both the effects of the heat generated as well as the targeted delivery to cancer cells can lead to much smaller overall doses of the anticancer drug needed to kill the cancer cells. Although this example is currently considered to be a useful embodiment, the general concepts of the current invention are not limited to this example.

Examples

The following examples help explain some concepts of the current invention. However, the general concepts of the current invention are not limited to the particular examples.

In these examples, we discuss four experiments performed on this magnetically-activated release system (MARS): 1) the macroscopic heating of the solution to induce guest release; 2) magnetic heating via application of an oscillating magnetic field as an external control; 3) localized magnetic heating without increasing solution temperature in thermostatted medium; and 4) remote-controlled actuation of the nanovalves to demonstrate controlled drug delivery in cancer cells.

Magnetic-core silica nanoparticles (MCSNs, see, e.g., FIG. 1) were synthesized by modifying a standard MCM-41-type synthesis.[2c] To contain the ZnNCs within the silica core, they were first stabilized in a surfactant solution. The silica precursor TEOS (tetraethyl orthosilicate) was added to a solution containing the CTAB-stabilized (cetyl trimethylammonium bromide) ZnNCs with sodium hydroxide. The base catalyzed the hydrolysis of the silica precursor to form the mesostructured nanoparticles around the ZnNCs. Particle characterization confirmed size and pore diameter, and inclusion of ZnNCs was confirmed by microscopy (Table 1, FIGS. 2A-2C and 3A-3D). To assemble the nanovalve for facilitation of magnetic actuation, a molecular machine was assembled on the particle. N-(6-N-aminohexyl)-aminomethyl triethoxysilane was first condensed on the particle surface. Cargo loading was accomplished by soaking the nanoparticles in a saturated solution of Rhodamine B or doxorubicin to fill the mesoporous structure by diffusion, resulting in a 4% loading by weight. Containment of cargo in the pores was achieved by adding cucurbit[6]uril, which electrostatically binds the molecular thread on the silica nanoparticle surface to the interior of the 1 nm cyclic cucurbit[6]uril cavity.[5b, 10] Following this step, the MARS were washed thoroughly with water to remove excess dye adsorbed on the silica surface.

TABLE 1

Dynamic light scattering data of the CTAB templated magnetic-core silica nanoparticles. The hydrodynamic radius is given as the mean.

| Rept. # | Mean (nm) | Std Dev. (nm) |
|---|---|---|
| Rept. 1 | 221.6 | 33.74 |
| Rept. 2 | 187.2 | 27.18 |
| Rept. 3 | 357.4 | 60.98 |
| Average | 255.4 | 40.63 |

Figure 5:
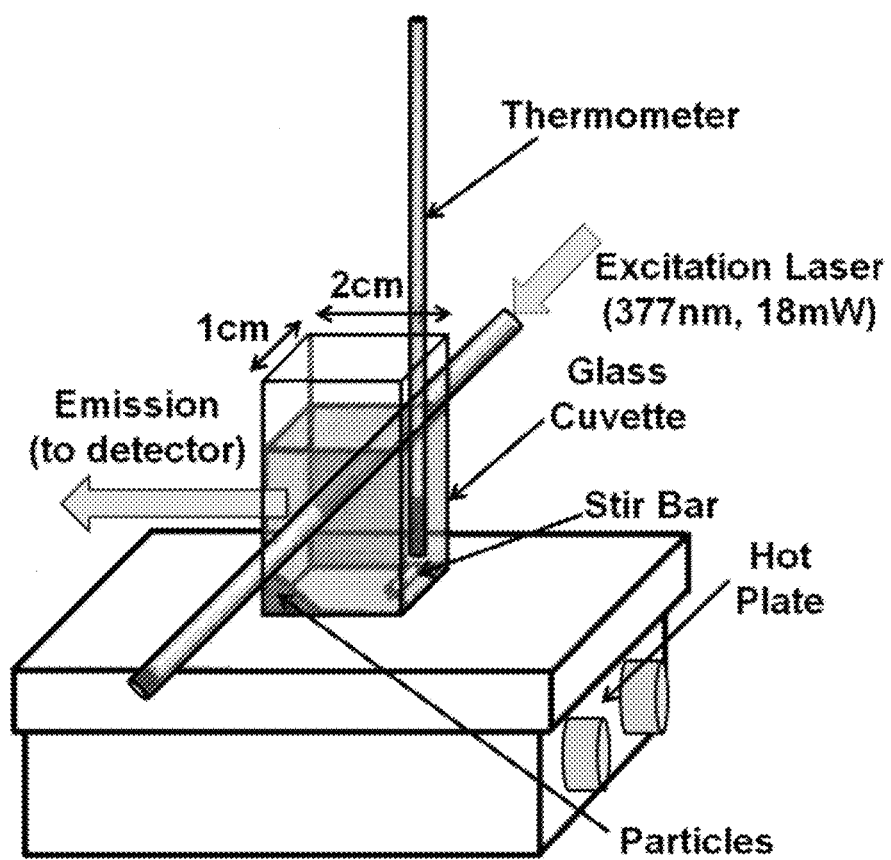
FIG. 5 shows an experimental setup for the external heating experiment. Particles are placed in one corner of the cuvette and DI water is added carefully to prevent particles from mixing into the solution. Stir bar is added and allowed to stir gently. An excitation laser is trained on the cuvette solution to excite release dye, in this case Rhodamine B, for detection by the CCD. The temperature is increased by directly heating the cuvette slowly on a hot plate. The volume of the water was small such that the water was heated relatively evenly. Additionally, the temperature was monitored at the top of the solution, away from the stir bar. For these studies, the nanoparticles were packed into the corner of the cuvette, and water was slowly added. Slow, gentle stirring does not redisperse the particles, allowing us to monitor dye release from the mesopores.

A nanovalve was selected for the MARS that remained closed at physiological temperature and opened when heated. The valve was attached to the surface of MSNs without magnetic cores and external heat was applied (FIG. 5). At room temperature, the valves remain closed and as the applied temperature is increased, dye is released.

Figure 6A:
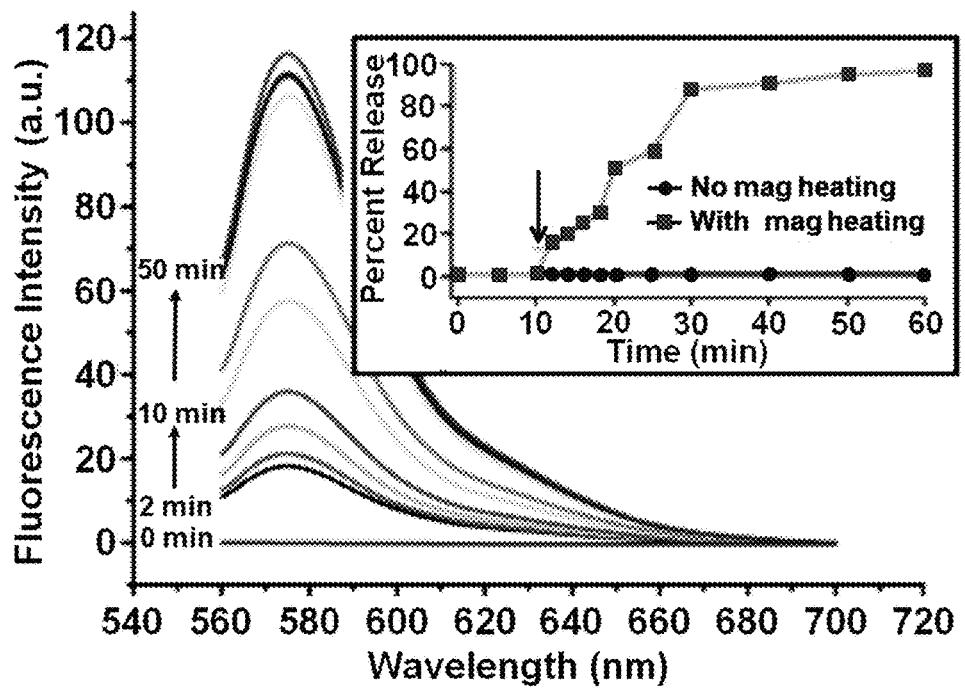
FIGS. 6A and 6B show cargo release using magnetic actuation according to an embodiment of the current invention. In (a), the MARS were continuously exposed to the magnetic field. The inset shows the data as a release profile. In (b), a sample was kept at 0° C. and exposed to pulses of the magnetic field. A single AC field exposure (circles) exhibited ~40% cargo release after an initial 1-minute pulse. Multiple pulses (squares, performed at 1, 3, 5, 7, and 9 minutes, then every 20 minutes for 270 minutes) enabled more dye release until all dye diffused out. A baseline (triangles) was obtained by monitoring the fluorescence with no pulse. The low temperature (0° C.) of the surrounding solution was maintained in order to observe the effects from the magnetic field only, and not from heating of the surrounding solution.

The complete MARS was tested to determine if magnetically induced heating opens the nanovalves, causing the release of contained fluorescent molecules. To perform this study, MARS particles at room temperature were placed into an oscillating magnetic field, and dye release was observed as a function of time. Although the source of heat was changed from an external source to the internal heating caused by magnetic actuation, dye release was still observed (FIG. 6A).

Figure 4:
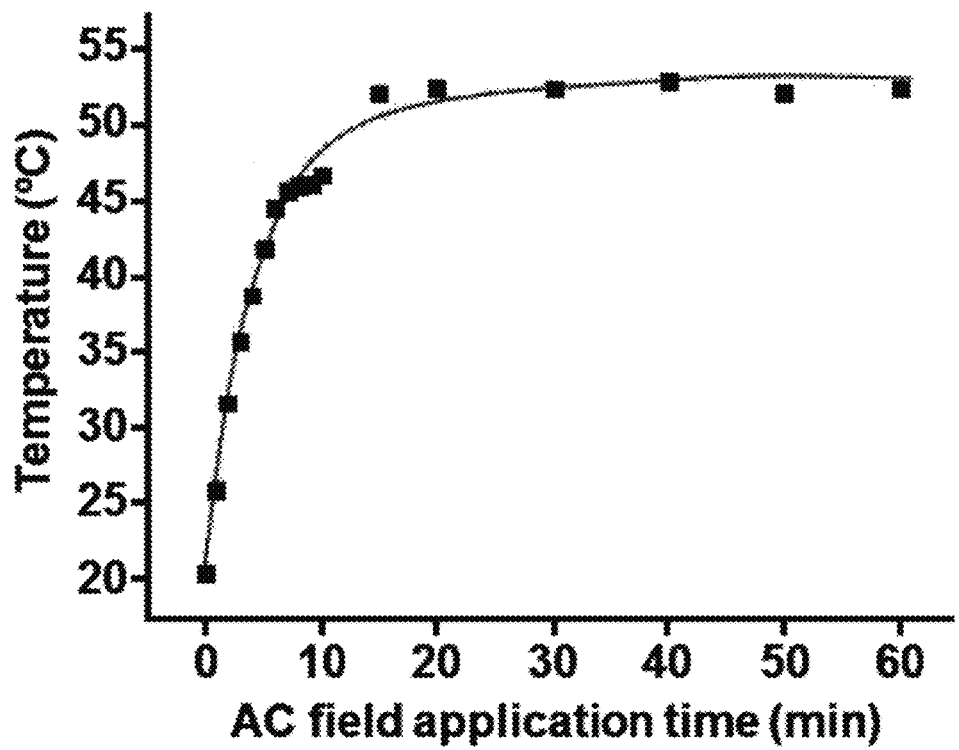
FIG. 4 shows heating profile of MCSNs in water. When 10 mg of MCSNs are placed in 1 mL of water and exposed to the oscillating magnetic field, the solution temperature increases as a function of the time exposed to the applied field. A maximum solution temperature of approximately 52° C. is reached after 15 minutes, and this temperature remains constant for the duration of the 60-minute experiment.

A sample of MCSNs was placed into an oscillating magnetic field to measure their effect on solution temperature. A sample at a concentration of 10 mg/mL was placed inside a water-cooled copper coil producing an alternating current magnetic field having a frequency of 500 kHz and a current amplitude of 37.4 kAm$^{-1}$ (Taeyang Instrument Company, Korea). The temperature of the water above the particles was monitored, and the 1 mL sample increased to a maximum temperature of 52° C. (FIG. 4). This effect is also observed for the ZnNCs in solution.[9]

TABLE 2

Heating studies of MCSNs with Rhodamine B in the pores.

| Maximum temperature (° C.) | Amount of dye released (compared to complete release) | Average heating rate (° C. min$^{-1}$) | Time to maximum amount released (s) |
|---|---|---|---|
| 21 | 0% | 0 | — |
| 41 | 30% | 4.72 | 3917 |
| 68 | 62% | 24.61 | 2800 |
| 83 | 100% | 42.41 | 1633 |

Figure 6B:
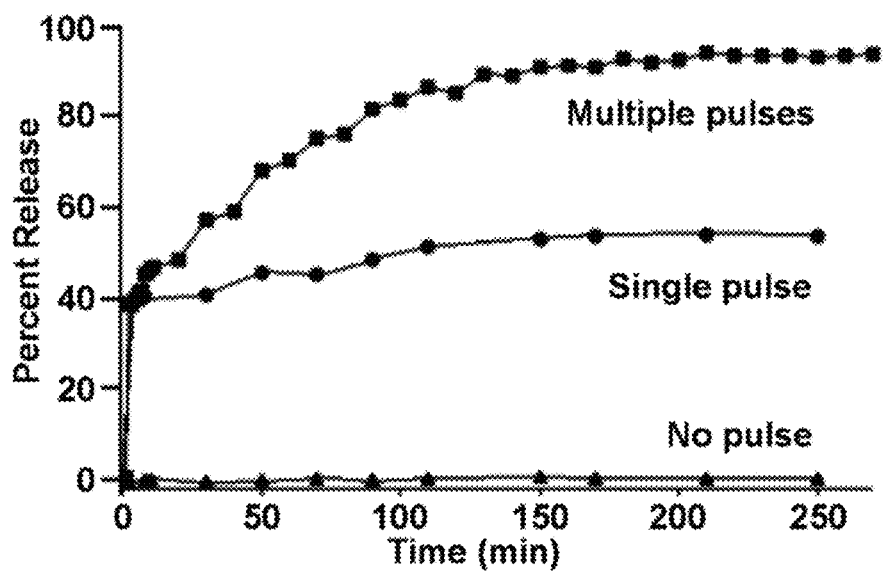

For therapeutic applications it is important to know if the opening of the nanovalve is a result of internal heating of the nanoparticle or an increase in the ambient temperature. The latter could result in necrosis instead of apoptosis from released drug. To determine if internal heating alone causes the valve to open, a sample of the MARS was kept at 0° C. and placed into the oscillating magnetic field. The MARS was then activated by applying one-minute pulses of the AC field while dye release was monitored using small aliquots of the particle solution placed in a fluorometer. A single pulse caused 40% of the Rhodamine B dye to be released with a dramatic increase in solution fluorescence (FIG. 6B, circle markers), which we attribute to rapid internal particle heating and valve opening. A second sample, pulsed intermittently, shows not only the same initial release of cargo, but also continued dye release upon each additional pulse (FIG. 6B, square markers). Under these conditions, it is clear that the local internal heating is important for dye release, and macroscopic heating of the bulk solution is not necessary for valve actuation.

Figure 7A:
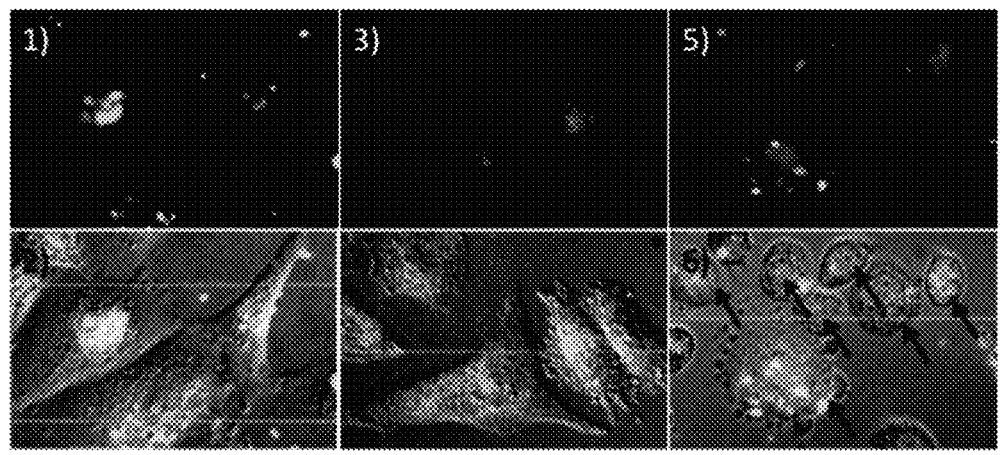
FIGS. 7A and 7B show results of MDA-MB-231 exposed to MARS. Figure (a) shows the fluorescent microscope images (1, 3, and 5) and the fluorescent images with differential interference contrast (2, 4, and 6). Green: fluorescently-labeled MARS, red: doxorubicin (DOX), yellow: merged green and red. MARS containing DOX were taken up into the cells, but before the AC field was applied, there was no drug released (images 1-2), and negligible cell death (~5%, figure b, left bar). Images 3 and 4 show the effects of the magnetic field on MARS without DOX in the pores. Heating from the particles accounts for 16% of the cell killing (figure b, middle bar). Images 5 and 6 demonstrate DOX release after a 5-minute AC field exposure, which caused 37% cell death (figure b, right bar). The arrows in image 6 indicate the location of apoptotic cells.

These materials are useful for in vitro drug delivery, as demonstrated by the release of anticancer drugs in the breast cancer cell line MDA-MB-231 (FIG. 7A). The MARS are taken up by the cells, and minimal drug release is observed because the surface-attached valves are closed (FIG. 7A, images 1-2). In the presence of the oscillating field, the local heating caused by the magnetic ZnNCs facilitated the release of doxorubicin from the silica pores, inducing apoptosis in the breast cancer cells (FIG. 7A, images 5-6). In the images taken after a five-minute exposure to the magnetic field, a dramatic increase in intensity from the doxorubicin (red color) was seen from the drug being delivered into the cells.

Figure 7B:
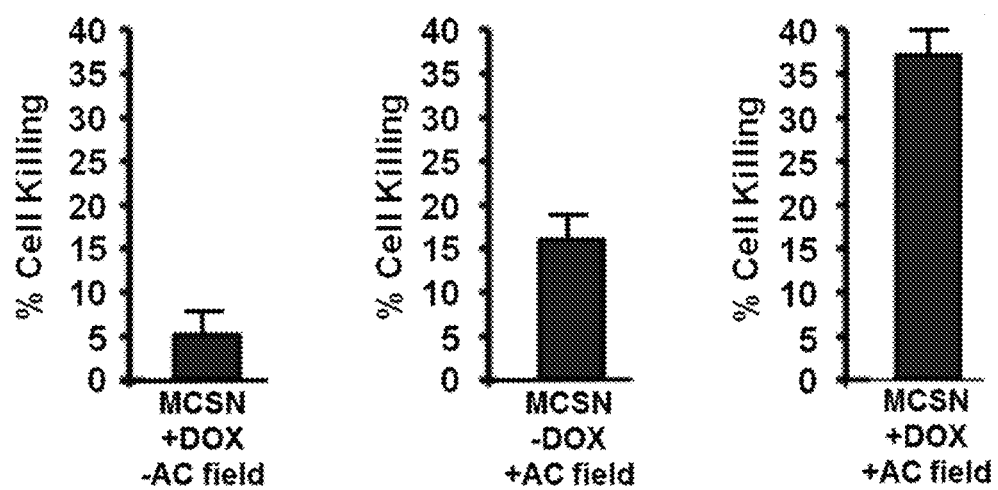

The effect of MARS on the cells was examined without drug loading under the same conditions as those with drug-loaded particles. When a sample not containing doxorubicin was endocytosed into the cells and exposed to the oscillating magnetic field, 16% cell killing was observed, while 37% cell killing resulted from exposure to the magnetic field when doxorubicin was contained in the mesopores (FIG. 7B). Thus both hyperthermia and drug delivery contributed to cell death.

In summary, we have demonstrated that novel magnetic-core silica nanoparticles are effective in actuating nanovalves and releasing anticancer drugs when exposed to an oscillating magnetic field. Additionally, we have shown the feasibility of this system to function as a drug delivery system in cancer cells. Optimization to balance the hyperthermic and apoptotic effects by varying the length of the magnetic actuation is under investigation.

Methods

Magnetic nanoparticles with Zn ion doped were synthesized using the method developed by Jang et al. (Jang, J.-T.; Nah, H.; Lee, J.-H.; Moon, S. H.; Kim, M. G.; Cheon, J. Angew. Chem. Int. Ed. 2009, 48, 1234-1238). A typical synthesis to produce $Zn_{0.4}Fe_{2.6}O_4$ nanoparticles is as follows: $ZnCl_2$ (30 mg), $FeCl_2$ (40 mg), and $Fe(acac)_3$ (353 mg) were placed in a 50 mL three-neck round-bottom flask in the presence of surfactants (oleic acid and oleylamine) in octyl ether. The reaction mixture was heated at 300° C. for 1 h and the reaction products were cooled to room temperature. Upon addition of ethanol, a black powder precipitated and was isolated by centrifugation. The isolated nanoparticles were dispersed in toluene. Nanoparticles have 15 nm size with narrow size distribution ($\sigma<5\%$).

Zinc-doped iron oxide nanocrystals were dissolved in chloroform at a concentration of 50 mg/mL. One milliliter of the iron oxide nanocrystals in chloroform was added to a solution of 100 mg cetyl trimethylammonium bromide (CTAB, Aldrich, 95%) in 5 mL of water. The mixture was sonicated and the chloroform was boiled off from the solution with rapid stirring. The aqueous CTAB stabilized zinc-doped iron oxide nanocrystals were added to an 80° C. solution of 43 mL distilled water with 350 μL of 2.0 M NaOH, and 500 μL tetraethyl orthosilicate (TEOS, Aldrich, 98%) was slowly added. After two hours of rapid stirring at 80° C., the magnetic-core silica nanoparticles were collected by centrifugation and washed with ethanol and water. The CTAB was removed by dispersing the as-synthesized materials in a solution containing 133.3 mg ammonium nitrate (Fisher) and 50 mL 95% ethanol. This mixture was heated to 60° C. for 15 minutes, then the particles were collected by centrifugation and washed with ethanol. Complete removal of the surfactant was verified by infrared spectroscopy. The fluorescent functionality for optical monitoring of the nanoparticles in cells, fluorescein isothiocyanate, was attached to the mesoporous silica framework. 3 mg fluorescein isothiocyanate (FITC, Sigma, 90%) was dissolved in 1 mL ethanol, and 12 μL 3-aminopropyltriethoxysilane (3-APTES, Aldrich, 98%) was added. This solution was reacted under nitrogen for 2 hours, then added to the 80° C. solution of aqueous sodium hydroxide. After 10 minutes, the CTAB-ZnNC solution was added, and the procedure followed in the same manner as above. These labeled particles were used in the biological studies to monitor the MARS in MDA-MB-231 cells.

The nanovalve was attached by refluxing 100 mg of the magnetic-core silica nanoparticles with $4\times10^{-4}$ mol N-(6-N-aminohexyl)-aminomethyl triethoxysilane in toluene overnight. The particles were collected by centrifugation and washed with methanol. To load dye or drug molecules into the particles, the particles were soaked in a saturated dye or drug solution for 24 hours. To the loading solution was added a solution containing 80 mg CB[6] in 5 mL of 1 mM HCl. The capping reaction continued stirring for 3 days, following which the particles were collected by centrifugation and washed with water until the supernatant was free of dye or drug.

A control experiment has been performed where nanoparticles are loaded with dye or drug molecules, but no capping group (i.e. cucurbit[6]uril, CB[6]) is added. These control particles were washed exactly as those with CB[6] were washed before studying the release. Since the capping group is not present in the control to contain the dye/drug within the pores, the dye is washed out during the washing step and there is no signal present in the release studies.

In another control experiment, particles that do not contain magnetic nanocrystals at the core were placed in the oscillating magnetic field. In this experiment, the particles cause no heating and no release of dye was observed.

The magnetic experiments were carried out as follows. Magnetic-core mesoporous silica nanoparticles (MCSNs) dispersed in water (1 mg/ml) were placed inside a water-cooled copper coil which produced an alternating magnetic field in frequency range of 500 kHz with an amplitude of up to 37.4 $kAm^{-1}$. For the thermostatted experiment, the sample solution was kept at 0° C. while the field was applied. The temperature was measured with a thermometer (TES-1307, TES, Taiwan) placed in the center of the sample. The amount of released dye by magnetic heating was measured as follows. Small aliquots (10 μL) of solution were taken and the fluorescence was measured with photoluminescence spectrometer (FP-6500, JASCO).

To study the MARS in vitro, we performed a simple hyperthermia test with MDA-MB-231 breast cancer cell line. The cells were cultivated in Dulbecco's Modified Eagle Medium (Invitrogen) supplemented with 10% fetal bovine serum (Invitrogen) and 25 mM HEPES. These cells were cultivated at 37° C. in 5% $CO_2$. 50 μg/mL solution of MCSNs in 1× Dulbecco's Phosphate Buffered Saline (Sigma-Aldrich) were treated to the MDA-MB-231 cells cultured on eight-well plates (2.5×104 cells per well). 24 hours after the transfection of MCSNs, the MDA-MB-231 cells were then washed three times with 1× Dulbecco's Phosphate Buffered Saline. The eight-well plate was placed inside alternating magnetic field system described above. After 5 minutes of magnetic field application, cell viability was measured with Cell Counting Kit-8 (Dojindo co.). First, the cell suspension (100 μL/well) was inoculated in a 96-well plate, and the plate was pre-incubated in a humidified incubator at 37° C., 5% $CO_2$. Then 10 μl of the CCK-8 solution was added to each well of the plate, and incubated for 3 h in the incubator. At last, the cell viability was measured at 450 nm with reduced WST-8(2-(2-methoxy-4-nitrophenyl)-3-(4-nitrophenyl)-5-(2,4-disulfophenyl)-2Htetrazolium, monosodium salt) using a microplate reader (Bio-Tek).

REFERENCES 1. (a) Slowing, I.; Trewyn, B. G.; Lin, V. S.-Y. *J. Am. Chem. Soc.* 2006, 128, 14792-14793; (b) Lu, J.; Liong, M.; Zink, J. I.; Tamanoi, F. *Small* 2007, 3, 1341-1346; (c) Slowing, I.; Trewyn, B. G.; Lin, V. S.-Y. *J. Am. Chem. Soc.* 2007, 129, 8845-8849; (d) Vallet-Regi, M.; Balas, F.; Arcos, D. *Angew. Chem., Int. Ed.* 2007, 46, 7548-7558; (e) Liong, M.; Lu, J.; Kovochich, M.; Xia, T.; Ruehm, S. G.; Nel, A. E.; Tamanoi, F.; Zink, J. I. *ACS Nano* 2008, 2, 889-896; (f) Rosenholm, J. M.; Meinander, A.; Peuhu, E.; Niemi, R.; Eriksson, J. E.; Sahlgren, C.; Lind, M. *ACS Nano* 2009, 3, 197-206.
2. (a) Lin, Y.-S.; Tsai, C.-P.; Huang, H.-Y.; Kuo, C.-T.; Hung, Y.; Huang, D.-M.; Chen, Y.-C.; Mou, C.-Y. *Chem. Mater.* 2005, 17, 4570-4573; (b) Lin, Y.-S.; Wu, S.-H.; Hung, Y.; Chou, Y.-H.; Chang, C.; Lin, M.-L.; Tsai, C.-P.; Mou, C.-Y. *Chem. Mater.* 2006, 18, 5170-5172; (c) Liong, M.; Lu, J.; Kovochich, M.; Xia, T.; Ruehm, S. G.; Nel, A. E.; Tamanoi, F.; Zink, J. I. *ACS Nano* 2009, 2, 889.
3. (a) Lai, C.-Y.; Trewyn, B. G.; Jeftinija, D. M.; Jeftinija, K.; Xu, S.; Jeftinija, S.; Lin, V. S.-Y. *J. Am. Chem. Soc.* 2003, 125, 4451-4459; (b) Giri, S.; Trewyn, B. G.; Stellmaker, M. P.; Lin, V. S.-Y. *Angew. Chem. Int. Ed.* 2005, 44, 5038-5044; (c) Aznar, E.; Marcos, M. D.; Martinez- Manez, R.; Sancenon, F.; Soto, J.; Amoros, P.; Guillem, C. *J. Am. Chem. Soc.* 2009, 131, 6833-6843; (d) Bernardos, A.; Aznar, E.; Marcos, M. D.; Martinez-Manez, R.; Sancenon, F.; Soto, J.; Barat, J. M.; Amoros, P. *Angew. Chem. Int. Ed.* 2009, 48, 5884-5887; (e) Schlossbauer, A.; Kecht, J.; Bein, T. *Angew. Chem. Int. Ed.* 2009, 48, 3092-3095; (g) Zhao, Y.; Trewyn, B. G.; Slowing, I. I.; Lin, V. S.-Y. *J. Am. Chem. Soc.* 2009, 131, 8398-8400; (f) Coti, K. K.; Belowich, M. E.; Liong, M.; Ambrogio, M. W.; Lau, Y. A.; Khatib, H. A.; Zink, J. I.; Khashab, N. M.; Stoddart, J. F. 2009, 1, 16-39.
4. (a) Zhu, Y.; Fujiwara, M. *Angew. Chem. Mt. Ed.* 2007, 46, 2241-2244; (b) Lu, J.; Choi, E.; Tamanoi, F.; Zink, J. I. *Small* 2008, 4, 421-426; (c) Mal, N. K.; Fujiwara, M.; Tanaka, Y. *Nature* 2003, 421, 350-353; (d) Ferris, D. P.; Zhao, Y.-L.; Khashab, N. M.; Khatib, H. A.; Stoddart, J. F.; Zink, J. I. *J. Am. Chem. Soc.* 2009, 131, 1686-1688; (e) Park, C.; Lee, K.; Kim, C. *Angew. Chem. Int. Ed.* 2009, 48, 1275-1278; (f) Vivero-Escoto, J. L.; Slowing, I. I.; Wu, C.-W.; Lin, V. S.-Y. *J. Am. Chem. Soc.* 2009, 131, 3462-3463; (g) Nguyen, T. D.; Leung, K. C.-F.; Liong, M.; Liu, Y.; Stoddart, J. F.; Zink, J. I. *Adv. Funct. Mater.* 2007, 17, 2101-2110.
5. (a) Park, C.; Oh, K.; Lee, S. C.; Kim, C. *Angew. Chem. Int. Ed.* 2007, 46, 1455-1457; (b) Angelos, S.; Khashab, N. M.; Yang, Y.-W.; Trabolsi, A.; Khatib, H. A.; Stoddart, J. F.; Zink, J. I. *J. Am. Chem. Soc.* 2009, 131, 12912-12914; (c). Leung, K. C.-F.; Nguyen, T. D.; Stoddart, J. F.; Zink, J. I. *Chem. Mater.* 2006, 18, 5919-5928.
6. (a) Nguyen, T. D.; Tseng, H.-R.; Celestre, P. C.; Flood, A. H.; Liu, Y.; Stoddart, J. F.; Zink, J. I. *Proc. Natl. Acad. Sci. U.S.A.* 2005, 102, 10029-10034; (b) Liu, R.; Zhao, X.; Wu, T.; Feng, P. *J. Am. Chem. Soc.* 2008, 130, 14418-14419; (c) Saha, S.; Johansson, E.; Flood, A. H.; Tseng, H.-R.; Zink, J. I.; Stoddart, J. F. *Chem. Euro. J.* 2005, 11, 6846-6858.
7. (a) Fortin, J.-P.; Wilhelm, C.; Servais, J.; Menager, C.; Bacri, J.-C.; Gazeau, F. *J. Am. Chem. Soc.* 2007, 129, 2628-2635; (b) Derfus, A. M.; Maltzahn, G.; Harris, T. J.; Duza, T.; Vecchio, K. S.; Ruoslahti, E.; Bhatia, S. N. *Adv. Mater.* 2007, 19, 3932-3936; (c) Hu, S.-H.; Chen, S.-Y.; Liu, D.-M.; Hsaio, C.-S. *Adv. Mater.* 2008, 20, 2690-2695.
8. (a) Weissleder, R.; Moores, A.; Mahmood, U.; Bhorade, R.; Benveniste, H.; Chiocca, E. A.; Basilion, J. P. *Nat. Med.* 2000, 6, 351-354; (b) Jun, Y.-W.; Lee, J.-H.; Cheon, J. *Angew. Chem. Int. Ed.* 2008, 47, 5122-5135; (c) Laurent, S.; Forge, D.; Port, M.; Roch, A.; Robic, C.; Elst, L. V.; Muller, R. N.; *Chem. Rev.* 2008, 108, 2064-2110; (d) Lee, J.-H.; Huh, Y.-M.; Jun, Y.-W.; Seo, J.-W.; Jang, J.-T.; Song, H.-T.; Kim, S.; Cho, E.-J.; Yoon, H.-G.; Suh, J.-S.; Cheon, *J. Nat. Med.* 2007, 13, 95-99.
9. Jang, J.-T.; Nah, H.; Lee, J.-H.; Moon, S. H.; Kim, M. G.; Cheon, *J. Angew. Chem., Int. Ed.* 2009, 48, 1234-1238.
10. (a) Mock, W. L. *Top. Curr. Chem.* 1995, 175, 1-24; (b) Kim, K. *Chem. Soc. Rev.* 2002, 31, 96-107; (c) Fusaro, L.; Locci, E.; Lai, A.; Luhmer, M. *J. Phys. Chem. B* 2008, 112, 15014-15020; (d) Masson, E.; Lu, X.; Ling, X.; Patchell, D. L. *Org. Lett.* 2009, 11, 3798-3801.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for controlled delivery of a substance into an animal or human body, said method comprising:
    administering a plurality of containment vessels into said animal or human body wherein:
        each of said containment vessels is comprised of a mesoporous silica nanoparticle defining a plurality of pores and each of said plurality of containment vessels has an average outer diameter less than about 1 µm;
        said mesoporous silica nanoparticle encapsulates a plurality of magnetic particles adapted to provide inductive heating when exposed to a time-varying magnetic field;
        each of said plurality of containment vessels comprises a quantity of said substance loaded into the pores of said mesoporous silica nanoparticle prior to said administering;
        each of said containment vessels comprises a plurality of heat-operable valve assemblies comprising:
            i) an alpha-cyclodextrin electrostatically bound to an adamantylethyl trichlorosilane attached to a surface of said vessel; or
            ii) a cucurbit[6]uril electrostatically bound to a N-(6-N-aminohexyl)aminomethyltriethoxysilane attached to a surface of said vessel;
    wherein said valve assemblies are structured so that in an absence of a time varying magnetic field and at normal temperatures of the animal or human body they retain said substance in said pores after said administering to prevent said quantity of said substance from being released from said pores;
    applying said time-varying magnetic field to induce heating of said containment vessels such that said heat-operable valve assemblies release at least a portion of said substance from said pores to deliver said substance into said animal or human body.

2. The method of claim 1, wherein the average outer diameter of each of said plurality of containment vessels administered is less than about 300 nm.

3. The method of claim 1, wherein the average outer diameter of each of said plurality of containment vessels administered is less than about 200 nm and greater than about 50 nm.

4. The method of claim 1, wherein each heat-operable valve assembly comprises a the cucurbit[6]uril electrostatically bound to the N-(6-N-aminohexyl)aminomethyltriethoxysilane attached to the surface of said vessel.

5. The method of claim 1, where each heat-operable valve assembly comprises the alpha-cyclodextrin electrostatically bound to the adamantylethyl trichlorosilane attached to the surface of said vessel.

6. The method of claim 1, wherein said substance comprises at least one substance selected from the group consisting of a cosmetic, a therapeutic, a nutritional agent, a diagnostic agent, and an anticancer drug.

7. The method of claim 1, wherein said substance comprises an anticancer drug.

8. The method of claim 7, wherein said drug is doxorubicin.

9. The method of claim 7, wherein said body is a living organism comprising cancer cells.

10. The method of claim 9, wherein said applying said time-varying magnetic field that induces heating of said containment vessels is performed after said plurality of containment vessels have entered into at least some of said cancer cells within said living organism such that said anticancer drug is released within said at least some cancer cells for cancer treatment.

11. The method of claim 9, wherein each of said containment vessels further comprises a coating to enhance uptake by said cancer cells preferentially over healthy cells.

12. The method of claim 1, wherein said magnetic particles comprise super paramagnetic nanoparticles.

13. The method of claim 12, wherein said super paramagnetic nanoparticles comprise zinc-doped iron oxide nanocrystals.

14. The method of claim 1, wherein each of said containment vessels further comprises a coating to enhance dispersion within a fluid medium substantially without aggregation.

15. The method of claim 1, wherein each of said containment vessels further comprises a coating to enhance dispersion within a fluid medium substantially without aggregation.

* * * * *